United States Patent
Okano et al.

(10) Patent No.: US 12,270,049 B2
(45) Date of Patent: Apr. 8, 2025

(54) DIFFERENTIATION-PROMOTED PLURIPOTENT STEM CELL AND USE THEREOF

(71) Applicant: KEIO UNIVERSITY, Tokyo (JP)

(72) Inventors: Hideyuki Okano, Tokyo (JP); Wado Akamatsu, Tokyo (JP); Koki Fujimori, Tokyo (JP); Takuya Matsumoto, Tokyo (JP); Naoko Kuzumaki, Tokyo (JP); Fumihiko Kisa, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 687 days.

(21) Appl. No.: 16/086,206

(22) PCT Filed: Mar. 27, 2017

(86) PCT No.: PCT/JP2017/012254
§ 371 (c)(1),
(2) Date: Nov. 28, 2018

(87) PCT Pub. No.: WO2017/170328
PCT Pub. Date: Oct. 5, 2017

(65) Prior Publication Data
US 2020/0299643 A1    Sep. 24, 2020

(30) Foreign Application Priority Data
Mar. 31, 2016 (JP) .................. 2016-073739

(51) Int. Cl.
*C12N 5/0797* (2010.01)
*C12N 5/10* (2006.01)

(52) U.S. Cl.
CPC ............ *C12N 5/0623* (2013.01); *C12N 5/10* (2013.01); *C12N 2501/115* (2013.01); *C12N 2501/15* (2013.01); *C12N 2501/155* (2013.01); *C12N 2501/235* (2013.01); *C12N 2501/727* (2013.01); *C12N 2506/02* (2013.01); *C12N 2506/45* (2013.01)

(58) Field of Classification Search
CPC .................................................. C12N 5/0623
See application file for complete search history.

(56) References Cited

U.S. PATENT DOCUMENTS

2015/0275171 A1    10/2015    Kato et al.
2015/0329821 A1    11/2015    Ang et al.

FOREIGN PATENT DOCUMENTS

| EP | 2821481 A1 | 1/2015 | |
|---|---|---|---|
| WO | WO-2013187416 A1 * | 12/2013 | ........... C12N 5/0623 |
| WO | 2014/069479 A1 | 5/2014 | |
| WO | 2014/161075 A1 | 10/2014 | |
| WO | WO 2015/034012 A1 | 3/2015 | |

OTHER PUBLICATIONS

Brown et al. (2010, PLoS One, vol. 5(6), e11373, pp. 1-9). (Year: 2010).*
Suemori et al. (2006, Biochemical and Biophysical Res. Comm., vol. 345, pp. 926-932). (Year: 2006).*
Supplementary European Search Report in related European Application No. EP 17774865.4, mailed Jan. 24, 2020 (8 pages).
Seki, T. et al., "Generation of induced pluripotent stem cells from human terminally differentiated circulating T cells," Cell Stem Cell, 7 (1), 11-14, 2010.
Li, W. et al., "Rapid induction and long-term self-renewal of primitive neural precursors from human embryonic stem cells by small molecule inhibitors," PNAS, vol. 108, No. 20, pp. 8299-8304, 2011.
International Search Report from PCT/JP2017/012254 dated Jun. 6, 2017.

* cited by examiner

*Primary Examiner* — Anoop K Singh
*Assistant Examiner* — David A Montanari
(74) *Attorney, Agent, or Firm* — Lathrop GPM; Brian Trinque; Tanya D'Souza

(57) ABSTRACT

A culture medium for inducing a pluripotent stem cell into a differentiation-promoted pluripotent stem cell, the medium including a Glycogen synthase kinase 3β (GSK3β) inhibitor, a Bone morphogenic protein (BMP) signaling inhibitor, and a Transforming growth factor (TGF)-β inhibitor as active ingredients.

8 Claims, 16 Drawing Sheets

DIFFERENTIATION-PROMOTED PLURIPOTENT STEM CELL AND USE THEREOF

TECHNICAL FIELD

The present invention relates to a differentiation-promoted pluripotent stem cell (Differentiating-state Stem Cell, hereinafter referred to as "DiSC" in some cases) and use thereof. In more detail, the present invention relates to a culture medium for inducing a pluripotent stem cell into a differentiation-promoted pluripotent stem cell, a method for manufacturing a differentiation-promoted pluripotent stem cell, a differentiation-promoted pluripotent stem cell, a method for manufacturing a neural stem cell mass, and a neural stem cell.

Priority is claimed on Japanese Patent Application No. 2016-073739, filed on Mar. 31, 2016, the content of which is incorporated herein by reference.

BACKGROUND ART

Induced pluripotent stem cells (hereinafter referred to as "iPSC" in some cases) have been produced from dermal fibroblasts in the related art. However, collection of skin is required in order to obtain a dermal fibroblast cell line, which is accompanied by problems such as bleeding, infection, and remaining scars.

Accordingly, a technique of producing iPSC from peripheral blood cells which can be collected with a less-invasive method is under examination. For example, it has been reported that CD3-positive T cells can be effectively reprogrammed into iPSC by using a Sendai virus vector (for example, refer to Non-Patent Document 1).

However, in general, characteristics of iPSC such as differentiation tendency greatly vary depending on types of cells, establishment methods, different donors, and the like which are used in establishing iPSC. Therefore, in the related art, it was necessary to select iPSC which easily differentiate into a desired cell among iPSC, requiring a lot of effort. In addition, the presence of an ES cell (embryonic stem cells, hereinafter referred to as "ESC" in some cases) line showing the resistance to differentiation has been known, and it was difficult to differentiate such ESC into a desired cell.

CITATION LIST

Non-Patent Literature

[Non-Patent Document 1] Seki T., et al., Generation of induced pluripotent stem cells from human terminally differentiated circulating T cells, Cell Stem Cell, 7 (1), 11-14, 2010.

SUMMARY OF INVENTION

Technical Problem

An object of the present invention is to provide a technique in which even the ES cell line showing the resistance to differentiation, and an iPS cell line immediately after establishment, which has not been selected by selection of cell lines can be effectively differentiated into a desired cell.

Solution to Problem

The present invention includes the following aspects.

(1) A culture medium for inducing a pluripotent stem cell into a differentiation-promoted pluripotent stem cell, the medium including, as active ingredients, a Glycogen synthase kinase 3β (GSK3β) inhibitor, a Bone morphogenic protein (BMP) signaling inhibitor, and a Transforming growth factor (TGF)-β inhibitor.

(2) A method for manufacturing a differentiation-promoted pluripotent stem cell, including culturing a pluripotent stem cell in the culture medium according to (1).

(3) The method for manufacturing a differentiation-promoted pluripotent stem cell according to (2), in which the pluripotent stem cell is not selected in advance according to origin, or a level of differentiation potential into endoderm, mesoderm, or ectoderm.

(4) A differentiation-promoted pluripotent stem cell, in which expression levels of endoderm, mesoderm, and ectoderm markers are increased compared with a control cell.

(5) The differentiation-promoted pluripotent stem cell according to (4), which is manufactured by the method for manufacturing according to (2) or (3).

(6) A differentiation-promoted pluripotent stem cell, in which a level of differentiation potential into endoderm, mesoderm, and ectoderm is improved compared with a control cell.

(7) The differentiation-promoted pluripotent stem cell according to (6), which is manufactured by the method for manufacturing according to (2) or (3).

(8) A method for manufacturing a neural stem cell mass, including culturing the differentiation-promoted pluripotent stem cell according to any one of (4) to (7) in a culture medium containing a GSK3β inhibitor, a TGF-β inhibitor, a Rho-associated protein kinase (ROCK) inhibitor, a Fibroblast Growth Factor 2 (FGF2), and a Leukemia Inhibitory Factor (LIF) as active ingredients.

(9) A neural stem cell mass, in which almost all neural stem cells constituting the neural stem cell mass do not substantially express an endoderm marker and a mesoderm marker.

(10) The neural stem cell mass according to (9), which is manufactured by the method for manufacturing according to (8).

(11) A method for manufacturing endoderm or tissue derived from the endoderm, including differentiating the differentiation-promoted pluripotent stem cell according to any one of (4) to (7).

(12) A method for manufacturing mesoderm or tissue derived from the mesoderm, including differentiating the differentiation-promoted pluripotent stem cell according to any one of (4) to (7).

(13) A method for manufacturing ectoderm or tissue derived from the ectoderm, including differentiating the differentiation-promoted pluripotent stem cell according to any one of (4) to (7).

[1] A culture medium for inducing a pluripotent stem cell into a differentiation-promoted pluripotent stem cell, the medium including a GSK3β inhibitor, a BMP signaling inhibitor, and a TGF-β inhibitor as active ingredients.

[2] A method for manufacturing a differentiation-promoted pluripotent stem cell, including culturing the pluripotent stem cell in the culture medium according to [1].

[3] A differentiation-promoted pluripotent stem cell, in which expression levels of endoderm, mesoderm, and ectoderm markers are increased compared with a control cell.

[4] A method for manufacturing a neural stem cell mass, including culturing the differentiation-promoted pluripotent stem cell according to [3] in a culture medium containing a GSK3β inhibitor, a TGF-β inhibitor, a ROCK inhibitor, a FGF2, and a LIF as active ingredients.

[5] A neural stem cell mass, in which almost all neural stem cells constituting the neural stem cell mass do not substantially express an endoderm marker and a mesoderm marker.

Advantageous Effects of Invention

According to the present invention, it is possible to provide a technique in which even the ES cell line showing the resistance to differentiation, and the iPS cell line immediately after establishment, which has not been selected by selection of cell lines can be effectively differentiated into a desired cell.

BRIEF DESCRIPTION OF DRAWINGS (a) to (g) of FIG. 1 are graphs showing an expression level of mRNA of each marker gene in Experimental Example 1. (a) shows the level of expression of OCT4, (b) shows the level of expression of NANOG, (c) shows the level of expression of SOX1, (d) shows the level of expression of PAX6, (e) shows the level of expression of NESTIN, (f) shows the level of expression of BRACHYURY, and (g) shows the level of expression of SOX17.

(a) to (g) of FIG. 2 are graphs showing an expression level of mRNA of each marker gene in Experimental Example 2. (a) shows the level of expression of OCT4, (b) shows the level of expression of NANOG, (c) shows the level of expression of SOX1, (d) shows the level of expression of PAX6, (e) shows the level of expression of NESTIN, (f) shows the level of expression of BRACHYURY, and (g) shows the level of expression of SOX17.

(a) of FIG. 3 is a representative optical photomicrograph of a human pluripotent stem cell colony (hPSC colony) maintaining an undifferentiated state. (b) is a representative optical photomicrograph of a hPSC colony underwent excessive differentiation. Magnifications of both (a) and (b) are the same, and a scale bar shows 200 μm.

FIG. 4 is a graph showing a proportion of hPSC colonies underwent the excessive differentiation among expressed hPSC colonies in a case where human iPSC were cultured in a culture medium added with SB, DM, and CHIR for 3 to 6 days to induce a differentiation-promoted pluripotent stem cell, in Experimental Example 2.

(a) of FIG. 5 is a representative optical photomicrograph of a normal iPSC colony in Experimental Example 3. (b) is a representative optical photomicrograph a differentiation-promoted pluripotent stem cell colony in Experimental Example 3. Magnifications of both (a) and (b) are the same, and a scale bar shows 200 μm.

Figure 10:
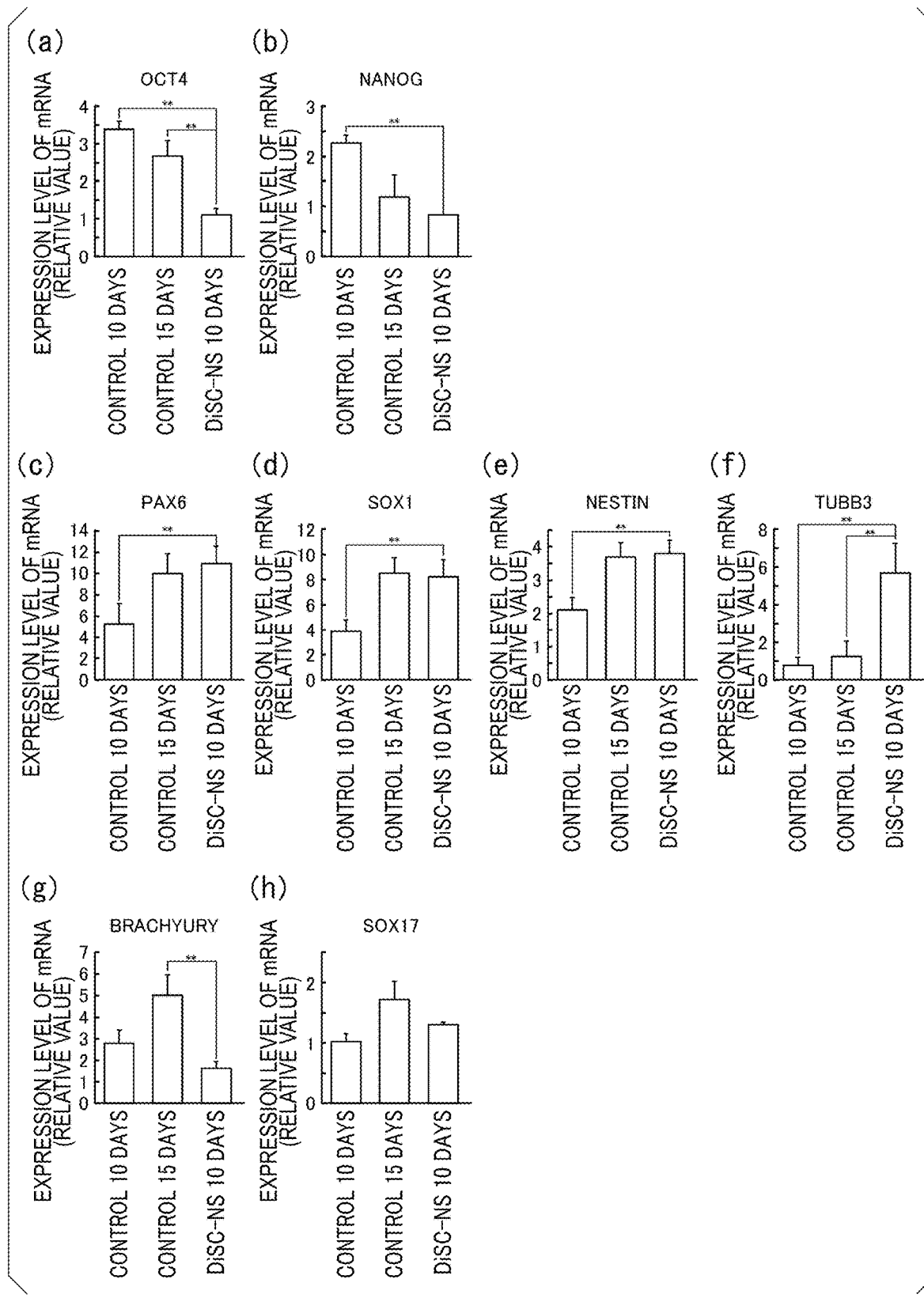

(a) to (h) of FIG. 10 are graphs showing an expression level of mRNA of each marker gene in Experimental Example 5. (a) shows the level of expression of OCT4, (b) shows the level of expression of NANOG, (c) shows the level of expression of PAX6, (d) shows the level of expression of SOX1, (e) shows the level of expression of NESTIN, (f) shows the level of expression of TUBB3, (g) shows the level of expression of BRACHYURY, and (h) shows the level of expression of SOX17.

Figure 11:
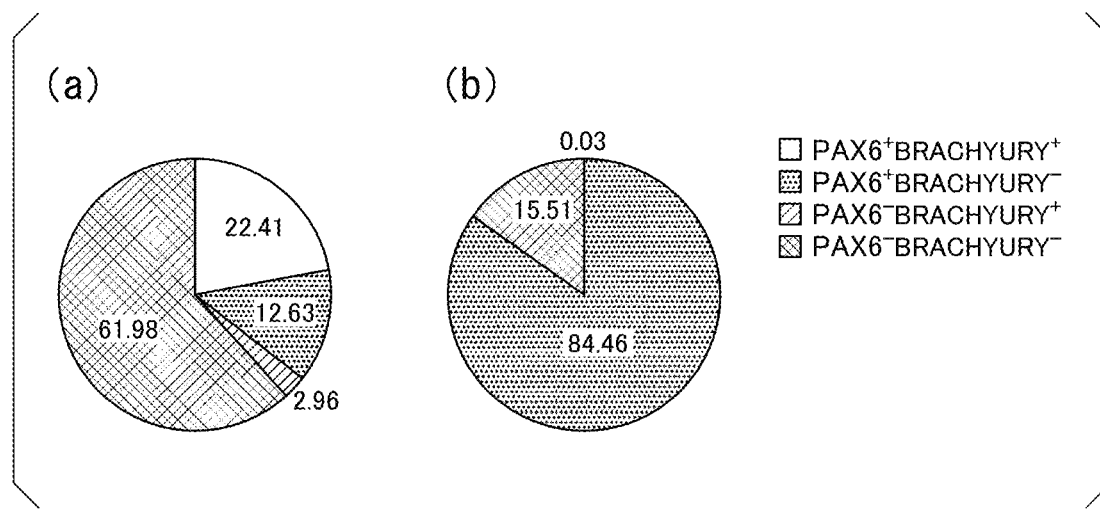

(a) of FIG. 11 is a graph showing percentages of PAX6$^+$BRACHYURY$^+$ cell, PAX6$^+$BRACHYURY$^-$ cell, PAX6$^-$BRACHYURY$^+$ cell, and PAX6$^-$BRACHYURY$^-$ cell in a neural stem cell mass formed not through the differentiation-promoted pluripotent stem cells in Experimental Example 5. (b) is a graph showing percentages of PAX6$^+$BRACHYURY$^+$ cell, PAX6$^+$BRACHYURY$^-$ cell, PAX6$^-$BRACHYURY$^+$ cell, and PAX6$^-$BRACHYURY$^-$ cell in a neural stem cell mass formed through the differentiation-promoted pluripotent stem cells in Experimental Example 5.

Figure 12:
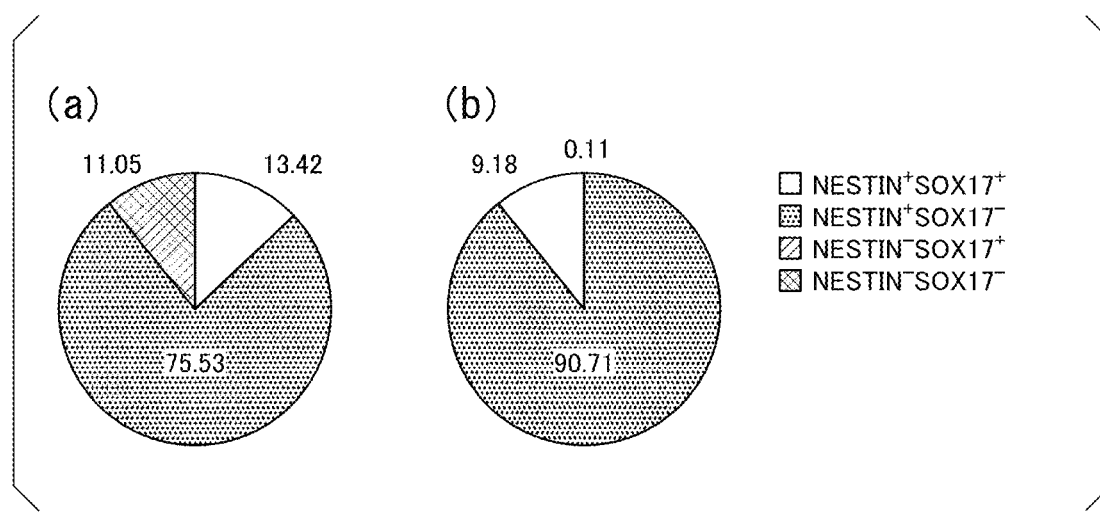

(a) of FIG. 12 is a graph showing percentages of NESTIN$^+$SOX17$^+$ cell, NESTIN$^+$SOX17$^-$ cell, NESTIN$^-$SOX17$^+$ cell, and NESTIN$^-$SOX17$^-$ cell in the neural stem cell mass formed not through the differentiation-promoted pluripotent stem cells in Experimental Example 5. (b) is a graph showing percentages of NESTIN$^+$SOX17$^+$ cell, NESTIN$^+$SOX17$^-$ cell, NESTIN$^-$SOX17$^+$ cell, and NESTIN$^-$SOX17$^-$ cell in the neural stem cell mass formed through the differentiation-promoted pluripotent stem cells in Experimental Example 5.

Figure 13:
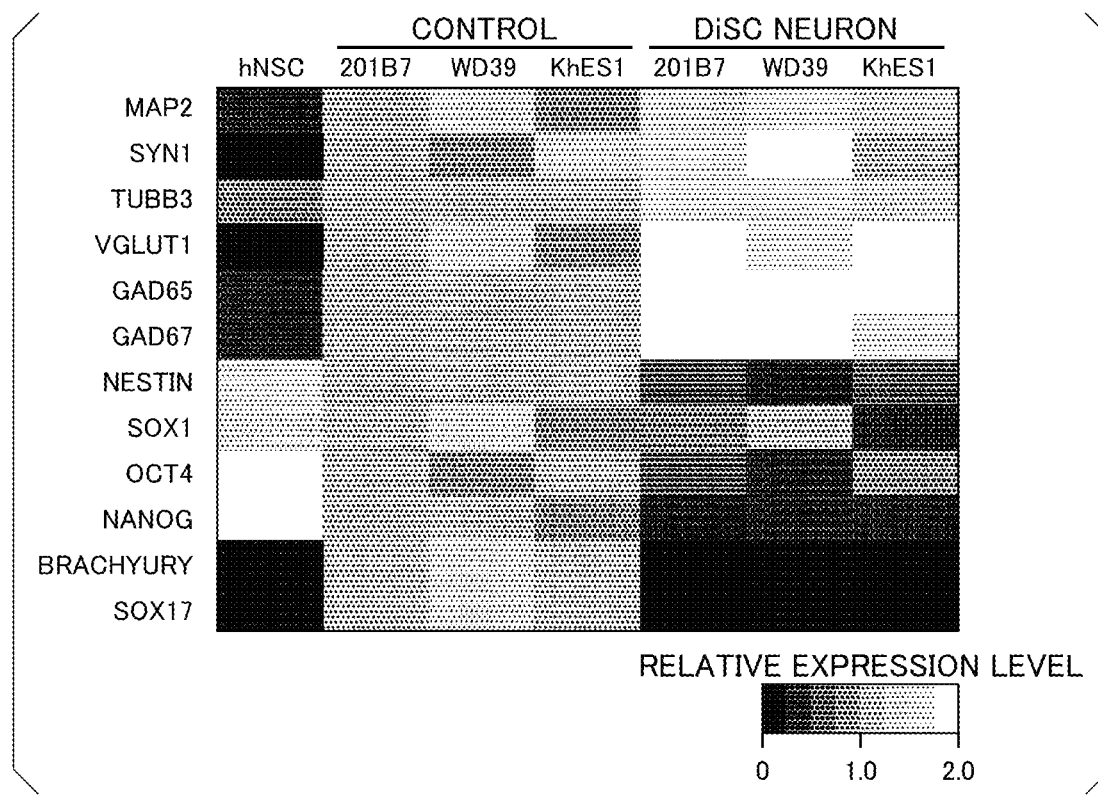

FIG. 13 is a graph showing results in which the neural stem cell mass formed through the differentiation-promoted pluripotent stem cells, or formed not through the differentiation-promoted pluripotent stem cells are further induced to be differentiated into neurons, and an expression level of each marker gene is measured in Experimental Example 6.

Figure 14:
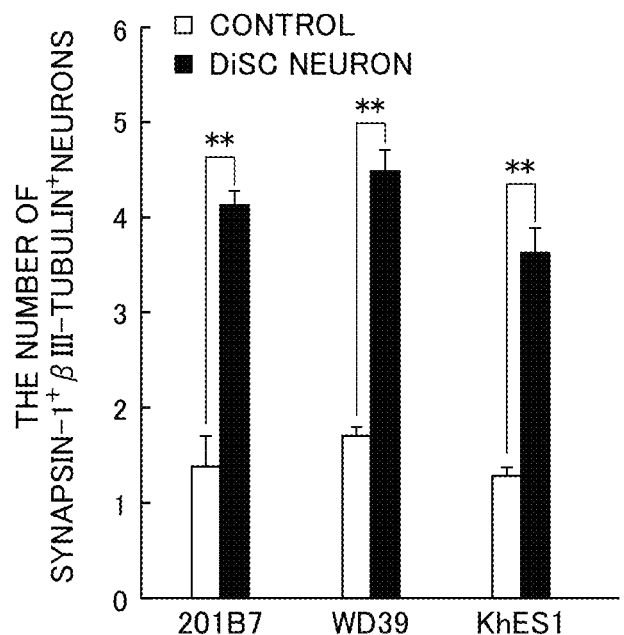

FIG. 14 is a graph showing the results of measuring the number of mature neurons in Experimental Example 7.

Figure 15:
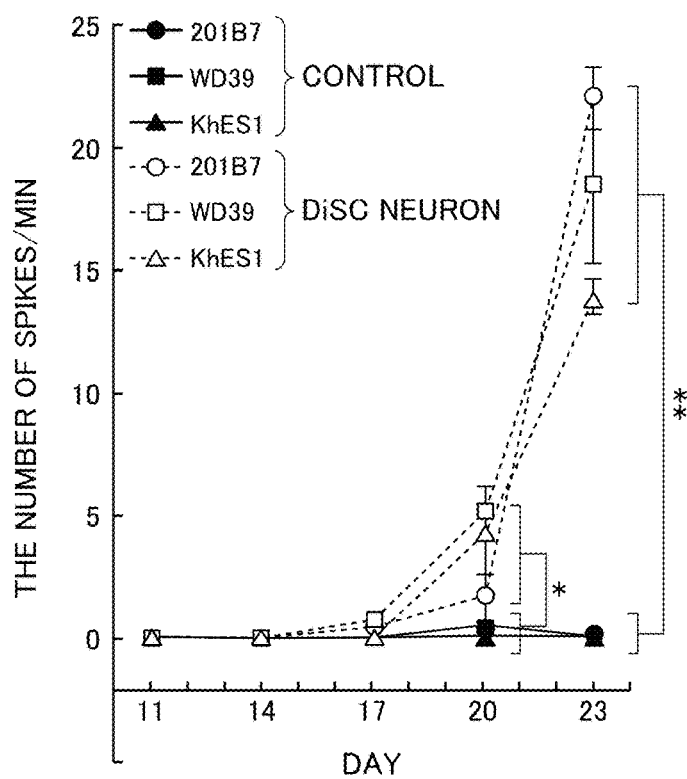

FIG. 15 is a graph showing the results of measuring the number of firing neurons in Experimental Example 8.

Figure 16:
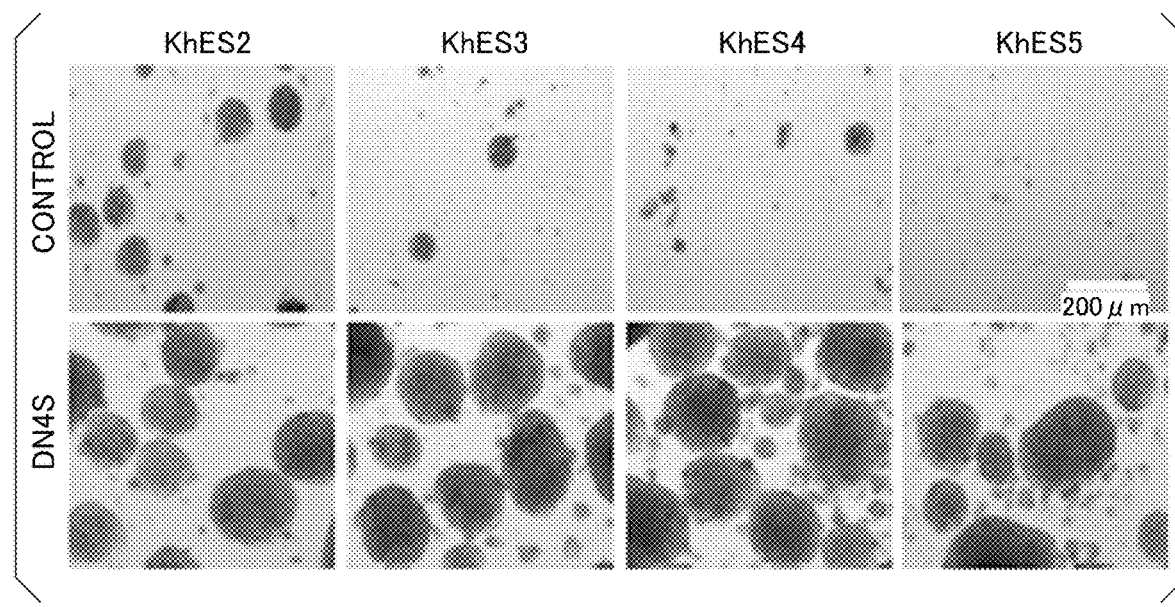

FIG. 16 shows optical photomicrographs of ES cells cultured under each condition in Experimental Example 9.

Figure 17:
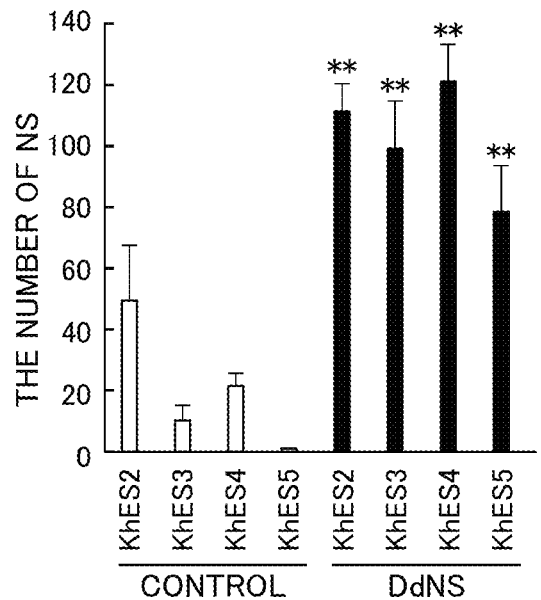

FIG. 17 is a graph showing the results of measuring the number of neural stem cell mass formed from the ES cells cultured under each condition in Experimental Example 9.

Figure 18:
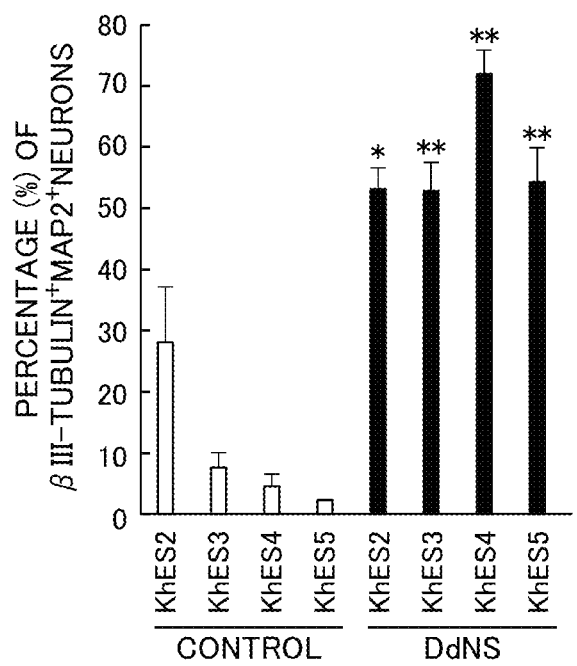

FIG. 18 is a graph showing the results of measuring the number of βIII-tubulin$^+$MAP2$^+$ neurons occupying the whole neurons in Experimental Example 10.

Figure 19:
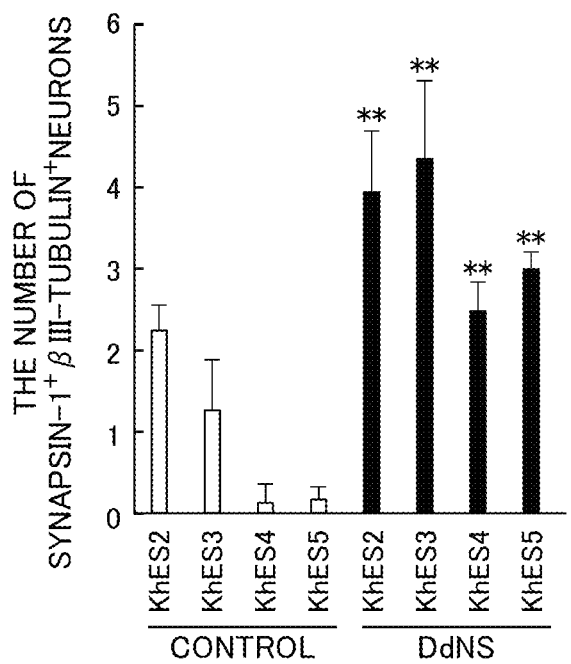

FIG. 19 is a graph showing the results of measuring the number of mature neurons in Experimental Example 10.

Figure 20:
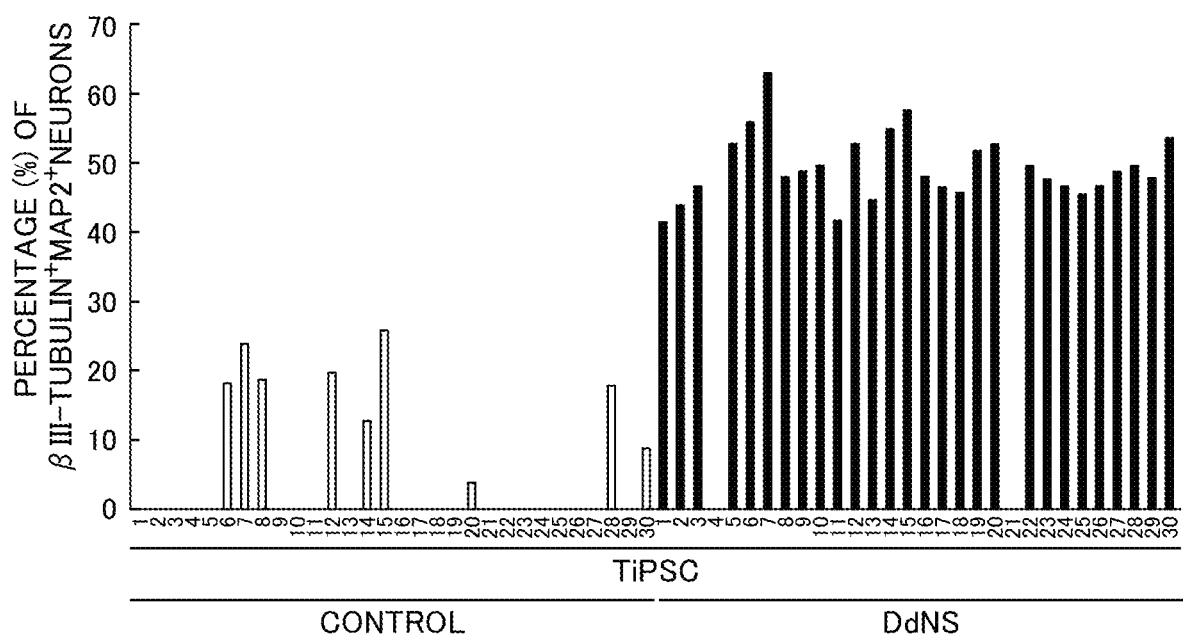

FIG. 20 is a graph showing the results of measuring the number of βIII-tubulin$^+$MAP2$^+$ neurons occupying the whole neurons in Experimental Example 11.

Figure 21:
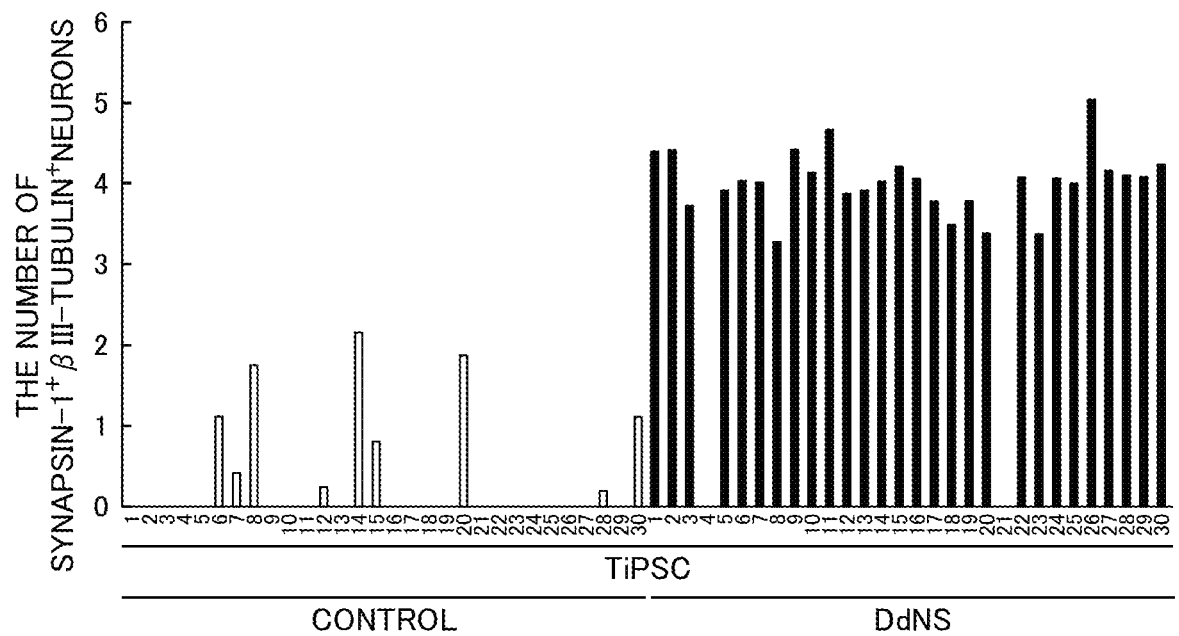

FIG. 21 is a graph showing the results of measuring the number of mature neurons in Experimental Example 11.

Figure 22:
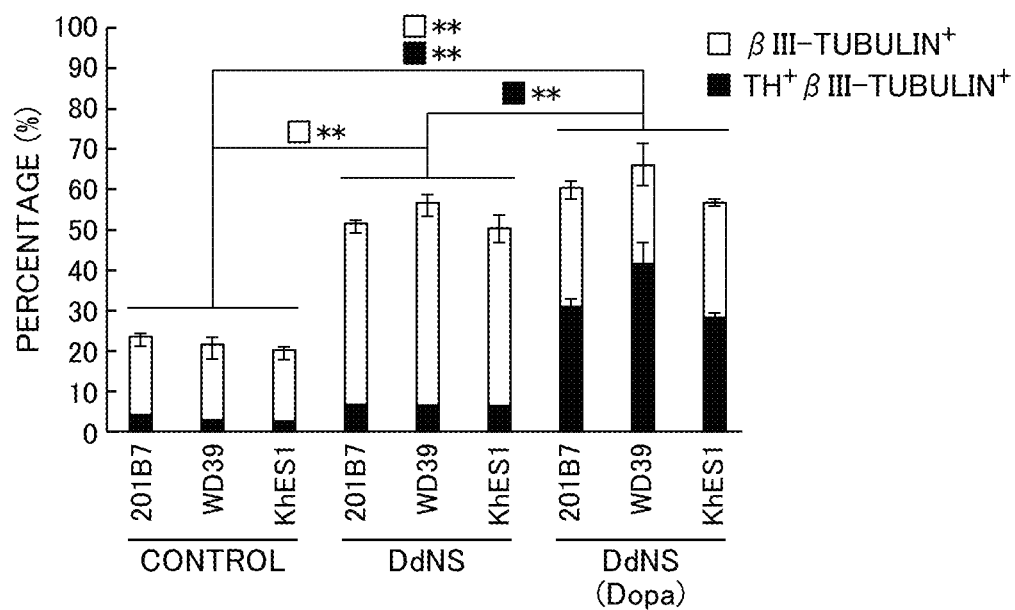

FIG. 22 is a graph showing the results of measuring percentages of βIII-tubulin$^+$ cell or TH$^+$βIII-tubulin$^+$ cell in Experimental Example 12.

Figure 23:
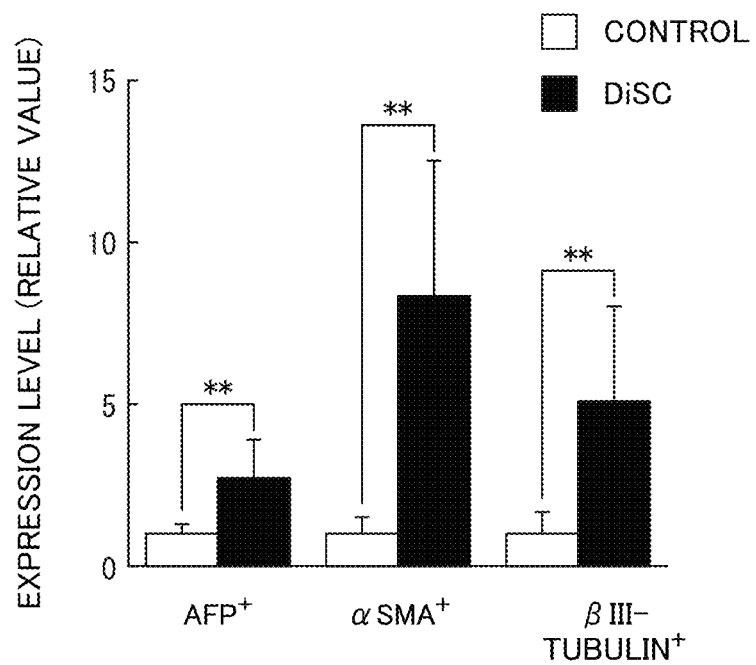

FIG. 23 is a graph showing the results of quantifying an expression level of differentiation markers of each cell in Experimental Example 13.

Figure 24:
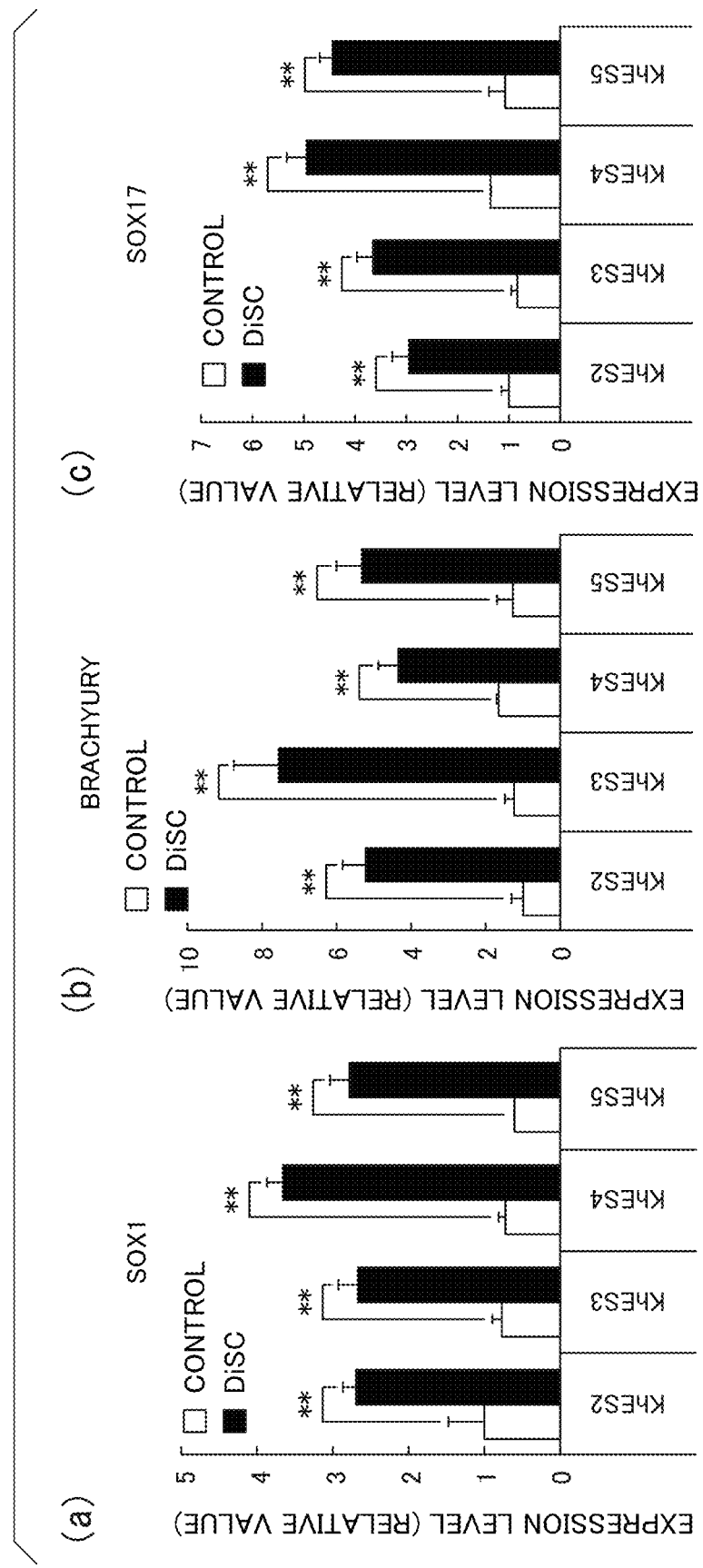

(a) of FIG. 24 is a graph showing the results of measuring an expression level of SOX1 protein of each cell in Experimental Example 14. (b) is a graph showing the results of measuring an expression level of BRACHYURY protein of each cell in Experimental Example 14. (c) is a graph showing the results of measuring an expression level of SOX17 protein of each cell in Experimental Example 14.

Figure 25:
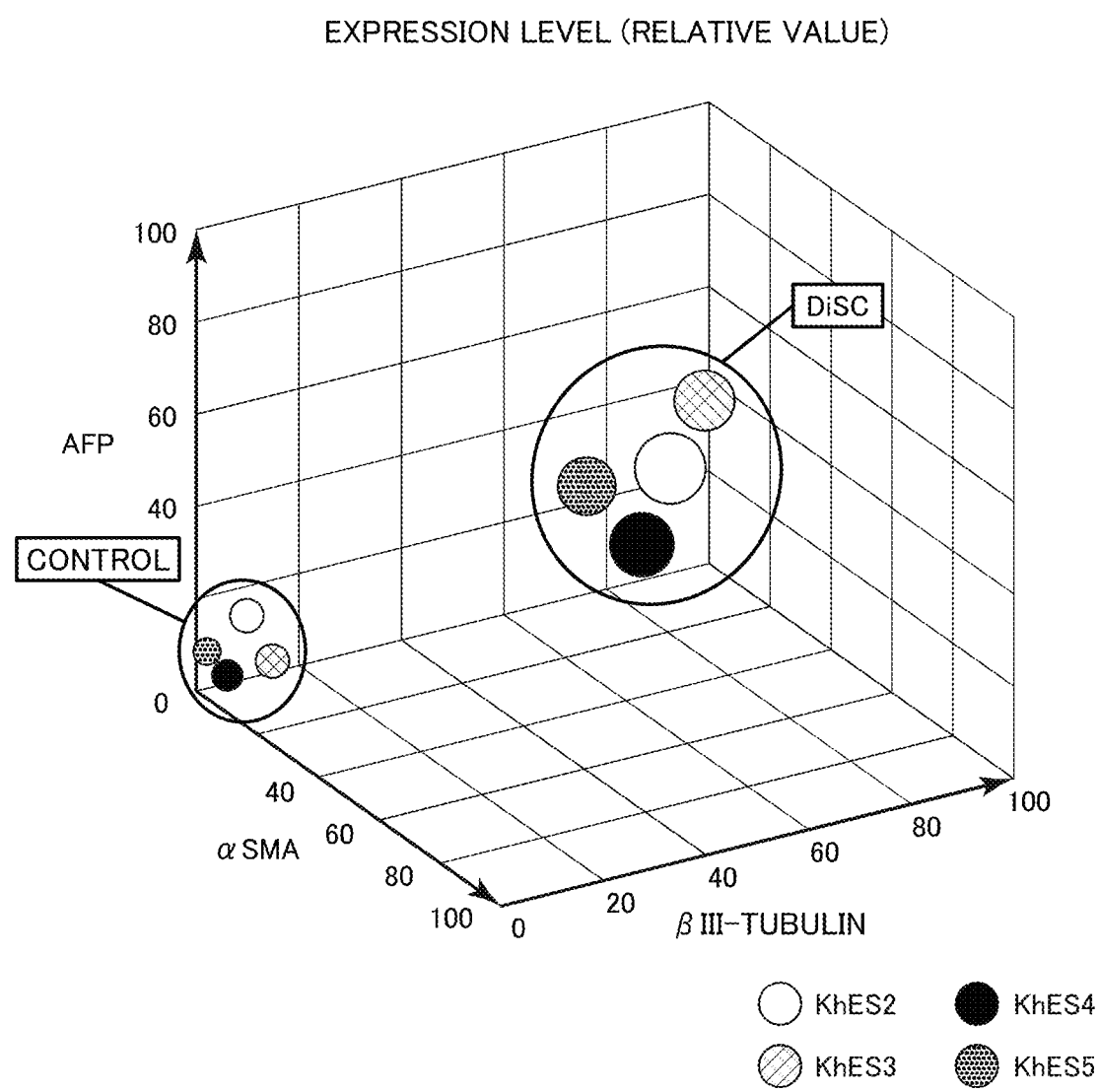

FIG. 25 is a graph showing the results of quantifying an expression level of differentiation markers of each cell in Experimental Example 14.

Figure 26:
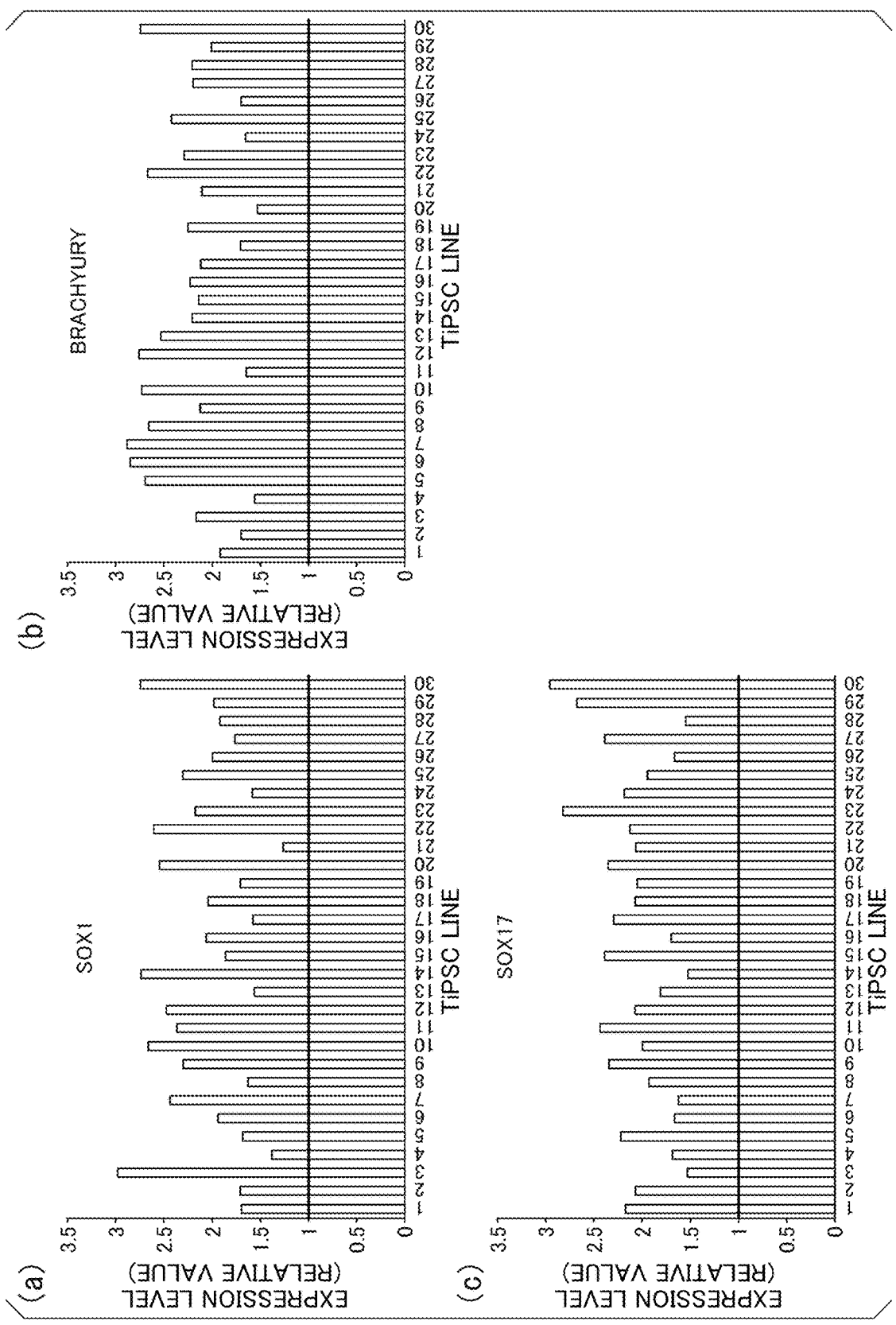

(a) of FIG. 26 is a graph showing the results of measuring an expression level of the SOX1 protein of each cell in Experimental Example 15. (b) is a graph showing the results of measuring an expression level of the BRACHYURY protein of each cell in Experimental Example 15. (c) is a graph showing the results of measuring an expression level of the SOX17 protein of each cell in Experimental Example 15.

DESCRIPTION OF EMBODIMENTS

[Culture Medium for Induction into Differentiation-Promoted Pluripotent Stem Cell]

In one embodiment, the present invention provides a culture medium for inducing a pluripotent stem cell into a differentiation-promoted pluripotent stem cell, the medium including a GSK3β inhibitor, a BMP signaling inhibitor, and a TGF-β inhibitor as active ingredients. The differentiation-promoted pluripotent stem cell referred herein is a cell newly found by the inventors of the present invention, in which expression levels of endoderm, mesoderm, and ectoderm markers increased while an undifferentiated state is maintained.

As will be described later in examples, the inventors of the present invention shed light on that the differentiation-promoted pluripotent stem cell can be induced from the pluripotent stem cell with the culture medium of the present embodiment. In addition, as will be described later in the examples, the inventors of the present invention shed light on that, by inducing the differentiation-promoted pluripotent stem cell from the pluripotent stem cell and differentiating the differentiation-promoted pluripotent stem cell into a desired cell, differentiation efficiency can be improved, and differentiation into a functional cell can be made in a short period of time for culturing compared with methods of the related art. Furthermore, the inventors of the present invention shed light on that, as the pluripotent stem cell, even an ES cell line showing the resistance to differentiation, and an iPS cell line immediately after establishment, which has not been selected by selection of cell lines can be induced into the differentiation-promoted pluripotent stem cell according to the culture medium of the present embodiment.

In the culture medium of the present embodiment, examples of the GSK3β inhibitor include CHIR99021 (CAS No. 252917-06-9). In addition, examples of the BMP signaling inhibitor include Dorsomorphin (CAS No. 866405-64-3), LDN-193189 (CAS No. 1062368-24-4), Noggin, and the like. Furthermore, examples of the TGF-β inhibitor include SB431542 (CAS No. 301836-41-9), A-83-01 (CAS No. 909910-43-6), and the like.

In the present specification, the term "differentiation-promoted pluripotent stem cell" means a pluripotent stem cell in which the differentiation is promoted while maintaining sternness. As will be described later in the examples, in the differentiation-promoted pluripotent stem cell, a level of differentiation potential into all germ layers of endoderm, mesoderm, and ectoderm (hereinafter referred to as "three germ layers" in some cases) is improved compared to pluripotent stem cells not underwent a method for manufacturing of the present embodiment.

In the culture medium of the present embodiment, the concentration of the GSK3β inhibitor is preferably about 3 μM. In addition, the concentration of the BMP signaling inhibitor is preferably about 3 to 6 μM. Furthermore, the concentration of the TGF-β inhibitor is preferably about 3 to 6 μM.

In the culture medium of the present embodiment, the pluripotent stem cell of a target to be differentiated may be, for example, the ES cell, and may be, for example, the induced pluripotent stem cell (iPSC). Furthermore, the pluripotent stem cell of the target to be differentiated may be the ES cell line showing the resistance to differentiation, and may be the iPS cell line immediately after establishment, which has not been selected by selection of cell lines. In the related art, it was difficult to differentiate these cell lines into a desired cell, but by using the culture medium of the present embodiment, even these cell lines can be differentiated into a desired cell.

That is, by using the culture medium of the present embodiment, the differentiation-promoted pluripotent stem cell having a high level of differentiation potential into the endoderm, the mesoderm, and the ectoderm can be obtained without selecting the pluripotent stem cell in advance based on origin, establishment methods, the level of differentiation potential into the endoderm, the mesoderm, or the ectoderm, and the like of the pluripotent stem cell.

The culture medium of the present embodiment may be provided as a liquid or may be provided as a powder. In addition, an aspect in which the GSK3β inhibitor, the BMP signaling inhibitor, or the TGF-β inhibitor are provided in a separate container and added to the culture medium when being used, may be adopted.

[Method for Manufacturing Differentiation-Promoted Pluripotent Stem Cell]

In one embodiment, the present invention provides a method for manufacturing the differentiation-promoted pluripotent stem cell, including a step of culturing the pluripotent stem cell in the culture medium described above.

The method for manufacturing of the present embodiment can be said to be a method for manufacturing the differentiation-promoted pluripotent stem cell for differentiation into the endoderm or tissue derived from the endoderm. Alternatively, the method for manufacturing of the present embodiment can be said to be a method for manufacturing the differentiation-promoted pluripotent stem cell for differentiation into the mesoderm or tissue derived from the mesoderm. Alternatively, the method for manufacturing of the present embodiment can be said to be a method for manufacturing the differentiation-promoted pluripotent stem cell for differentiation into the ectoderm or tissue derived from the ectoderm.

Alternatively, the method for manufacturing of the present embodiment can be said to a method for manufacturing the differentiation-promoted pluripotent stem cell for differentiation into the endoderm or tissue derived from the endoderm, or for differentiation into the mesoderm or tissue derived from the mesoderm.

Examples of the tissue derived from the endoderm include esophagus epithelium, gastric epithelium, gastrointestinal epithelium, liver, pancreas, bladder epithelium, posterior urethral epithelium, tonsil, pharyngeal epithelium, laryngeal epithelium, tracheal epithelium, lung, thyroid, parathyroid gland, thymus, eustachian tube, tympanic cavity, and the like. In addition, examples of the tissue derived from the mesoderm include microglia, bone, cartilage, heart, vascular endothelium, blood cells, spleen, bone marrow, dentine, peritoneal epithelium, kidney, urinary tract, pleural epithelium, adrenal cortex, muscle, ovary, uterus, testis, connective tissue, and the like. Furthermore, examples of the tissue derived from the ectoderm include central neuron, peripheral neuron, neuron cells, axis cylinders, myelin sheath, oral epithelium, tongue, tooth enamel, external rectal epithelium, external urethral epithelium, nasal epithelium, pituitary gland, pineal gland, adrenal medulla, pupillary sphincter, pupillary dilator, skin, cornea, retina, inner ear, outer ear, vaginal epithelium, and the like.

In the method for manufacturing of the present embodiment, the pluripotent stem cell of the target to be differentiated may be, for example, the ES cell, and may be, for example, the induced pluripotent stem cell (iPSC), and furthermore, may be the ES cell line showing the resistance to differentiation, and may be the iPS cell line immediately after establishment, which has not been selected by selection of cell lines.

That is, according to the method for manufacturing of the present embodiment, the differentiation-promoted pluripotent stem cell having a high level of differentiation potential into all germ layers of the endoderm, the mesoderm, and the ectoderm can be obtained without selecting the pluripotent stem cell in advance based on origin, establishment methods, the level of differentiation potential into the endoderm, the mesoderm, or the ectoderm, and the like of the pluripotent stem cell. The method for manufacturing of the present embodiment can be a method by which the differentiation potential of the pluripotent stem cell into the endoderm, the mesoderm, and the ectoderm is improved, irrespective of origin of the pluripotent stem cell. Herein, the phrase "irrespective of origin" means that the differentiation potential is not affected by tissue from which the pluripotent stem cell is derived, a method for establishing the induced pluripotent stem cell, a vector used for establishing the induced pluripotent stem cell, a method for culturing the (induced) pluripotent stem cell, and the like.

As will be described later in the examples, the differentiation-promoted pluripotent stem cell can be manufactured by culturing the pluripotent stem cell in the culture medium described above. As will be described later in the examples, by differentiating the differentiation-promoted pluripotent stem cell into a desired cell, the differentiation efficiency can be improved, or differentiation into a functional cell can be made in a short period of time for culturing compared to a case in which a normal pluripotent stem cell is differentiated into a desired cell.

In the method for manufacturing of the present embodiment, a period of time for culturing the pluripotent stem cell in the culture medium described above is preferably for 4 to 6 days, and more preferably for 5 days. As will be described later in the examples, the differentiation-promoted pluripotent stem cell in which the expression levels of the endoderm, mesoderm, and ectoderm markers increased while maintaining the undifferentiated state, tends to be easily obtained with the period of time for culturing described above.

[Differentiation-Promoted Pluripotent Stem Cell]

In one embodiment, the present invention provides the differentiation-promoted pluripotent stem cell, in which the expression levels of the endoderm, mesoderm, and ectoderm markers are increased compared with a control cell. Examples of the control cell include a pluripotent stem cell not underwent to the step of being cultured in the culture medium described above. As will be described later in the examples, in the differentiation-promoted pluripotent stem cell of the present embodiment, the level of differentiation potential into all germ layers of the endoderm, the mesoderm, and the ectoderm is improved compared to the control cell.

It can be said that the differentiation-promoted pluripotent stem cell of the present embodiment is for the differentiation into the endoderm or the tissue derived from the endoderm. Alternatively, it can be said that the differentiation-promoted pluripotent stem cell of the present embodiment is for the differentiation into the mesoderm or the tissue derived from the mesoderm. Alternatively, it can be said that the differentiation-promoted pluripotent stem cell of the present embodiment is for the differentiation into the ectoderm or the tissue derived from the ectoderm.

Alternatively, it can be said that the differentiation-promoted pluripotent stem cell of the present embodiment is for differentiation into the endoderm or the tissue derived from the endoderm, or for differentiation into the mesoderm or the tissue derived from the mesoderm.

In the differentiation-promoted pluripotent stem cell of the present embodiment, expression of a marker for undifferentiated cells is maintained. Examples of the marker for undifferentiated cells include octamer-binding transcription factor 4 (OCT4), NANOG, and the like. In addition, examples of the endoderm marker include SOX17 and the like. Furthermore, examples of the mesoderm marker include BRACHYURY and the like. Furthermore, examples of the ectoderm marker include SOX1, PAX6, NESTIN, and the like. Expression levels of each marker may be measured in terms of mRNA levels, or may be measured in terms of protein levels.

[Method for Manufacturing Neural Stem Cell Mass]

In one embodiment, the present invention provides a method for manufacturing a neural stem cell mass, including a step of culturing the differentiation-promoted pluripotent stem cell described above in a culture medium containing the GSK3β inhibitor, the TGF-β inhibitor, a Rho-associated protein kinase (ROCK) inhibitor, a Fibroblast Growth Factor 2 (FGF2), and a Leukemia Inhibitory Factor (LIF) as active ingredients. The method for manufacturing of the present embodiment can be said to be a method for manufacturing a neural stem cell.

In a case where the neural stem cell mass is produced from the pluripotent stem cells, a differentiation induction method through formation of embryoid body (EB) of the related art requires about 1.5 months. With respect to the above method, differentiation of the pluripotent stem cell into the neural stem can be carried out within about 10 days according to the method for manufacturing of the present embodiment.

In addition, as will be described later in the examples, according to the method for manufacturing of the present embodiment, even the ES cell line showing the resistance to differentiation, and the iPS cell line immediately after establishment, which has not been selected by selection of cell lines, which were difficult to be differentiated into the nervous system by methods of the related art, can be highly-efficiently differentiated into the neural stem cell mass.

In the method for manufacturing of the present embodiment, regarding the GSK3β inhibitor, the TGF-β inhibitor, the same as described above applies. In addition, in the method for manufacturing of the present embodiment, in a case where the pluripotent stem cell of the target to be differentiated is a cell derived from humans, FGF2 and LIF are preferably derived from humans, and the GSK3β inhibitor, the TGF-β inhibitor, and the ROCK inhibitor are also preferably those intended for human ROCK. Furthermore, for example, in a case where the pluripotent stem cell of the target to be differentiated is a cell derived from mice, FGF2 and LIF are preferably derived from mice, and the GSK3β inhibitor, the TGF-β inhibitor, and the ROCK inhibitor are also preferably those intended for mouse ROCK.

Note that, RefSeq ID of human FGF2 protein is NP_001997, and RefSeq ID of mouse FGF2 protein is NP_032032. In addition, RefSeq ID of human LIF protein is NP_001244064, and RefSeq ID of mouse LIF protein is NP_001034626. The concentration of FGF2 in the culture medium described above is preferably about 20 ng/mL. In addition, the concentration of LIF in the culture medium described above is preferably about 10 ng/mL.

Examples of the ROCK inhibitor include Y27632 and the like. The concentration of the ROCK inhibitor in the culture medium described above is preferably about 10 μM.

In a case where the neural stem cell is induced from the differentiation-promoted pluripotent stem cell in the method for manufacturing of the present embodiment, the neural stem cells form the neural stem cell mass (neurosphere, hereinafter referred to as "NS" in some cases). The formed neural stem cell mass is dissociated into cells one by one, and the cells are cultured again in the culture medium containing the GSK3β inhibitor, the TGF-β inhibitor, the ROCK inhibitor, FGF2, and LIF as active ingredients, and thus can be subcultured in the state of the neural stem cells.

In the method for manufacturing of the present embodiment, the step of culturing the differentiation-promoted pluripotent stem cell in the culture medium described above is preferably performed under a low oxygen environment. As the low oxygen environment, there is an environment in which an oxygen concentration is, for example, 1% to 10% (v/v), and is, for example, 1% to 5% (v/v). Accordingly, the number of neural stem cell manufactured can be increased.

In addition, the method for manufacturing of the present embodiment preferably includes a step of dissociating the differentiation-promoted pluripotent stem cells into cells one by one, before the step of culturing the pluripotent stem cell in the culture medium described above. Accordingly, the number of neural stem cell manufactured can be increased.

[Neural Stem Cell Mass]

In one embodiment, the present invention provides the neural stem cell mass, in which almost all neural stem cells constituting the neural stem cell mass do not substantially express the endoderm marker and the mesoderm marker. In other words, the neural stem cell mass of the present embodiment can be referred to as a neural stem cell mass which substantially does not contain cells expressing the endoderm and mesoderm markers (which substantially does not contain cells expressing the endoderm marker and cells expressing the mesoderm marker), or as a neural stem cell mass which substantially does not contain cells expressing the endoderm marker and cells expressing the mesoderm marker, and which is derived from the pluripotent stem cells. The neural stem cell mass of the present embodiment can be manufactured by the method for manufacturing the neural stem cell mass described above.

Regarding the endoderm marker and the mesoderm marker, the same as described above applies. As will be described later in the examples, it became clear that, in the neural stem cell mass manufactured by the method for manufacturing the neural stem cell mass described above, the endoderm marker and the mesoderm marker are hardly expressed.

The neural stem cell mass is a cluster of cells formed by self-proliferation of neural stem cells which are cells of the ectodermal system, and therefore, generally, the neural stem cell mass in vivo does not express the endoderm marker and the mesoderm marker. However, in the neural stem cell mass obtained by differentiation induction of the pluripotent stem cell thereinto by the methods of the related art, there is a case where the cells expressing the endoderm marker or the mesoderm marker are mixed therein.

This is because, the neural stem cell mass obtained by differentiation induction of the pluripotent stem cell thereinto by the methods of the related art is constituted of a heterogeneous cell population such as (1) cells of the ectodermal system, (2) pluripotent cells that are committed to the ectodermal system, and (3) simply proliferated cells of the mesodermal system or cells of the endodermal system. Such a neural stem cell mass is difficult to be differentiated into functional neurons in some cases.

With respect to the above case, the neural stem cell mass of the present embodiment is constituted almost only of a cell population such as (1) cells of the ectodermal system, and (2) pluripotent cells that are committed to the ectodermal system. Therefore, the neural stem cell mass of the present embodiment can be said to be a highly pure neuronal differentiation-inducing base.

That is, according to the method for manufacturing a neural stem cell mass described above, the neural stem cell mass which almost does not contain the cells expressing the endoderm marker or the mesoderm marker. Almost all cells constituting the neural stem cell mass do not substantially express the endoderm marker and the mesoderm marker. Herein, the phrase "do not substantially express" means that, for example, in a case where the neural stem cell mass is dissociated into cells one by one, and the analysis of cell populations is performed, the cells expressing the endoderm marker and the mesoderm marker can hardly be detected. More specifically, the phrase means that a proportion of the cells expressing the endoderm marker and the mesoderm marker is, for example, 1% or lower. Note that, in the present specification, the analysis of cell populations refers to an analysis method for analyzing the expression of a marker protein for each immunostained cell.

In the neural stem cell constituting the neural stem cell mass described above, T cell receptor gene may be rearranged. The rearrangement of the T cell receptor gene indicates that the neural stem cell is derived from mature T cells.

That is, in the neural stem cell mass manufactured using iPSC produced from the mature T cell (hereinafter referred to as "TiPSC" in some case) as a material by the method for manufacturing the neural stem cell mass described above, the T cell receptor gene is rearranged.

[Method for Manufacturing Germ Layers or Tissue Thereof]

In one embodiment, the present invention provides the method for manufacturing the germ layers or the tissue thereof, including a step of differentiating the differentiation-promoted pluripotent stem cell described above. Examples of the germ layers or the tissue thereof include the endoderm or the tissue derived from the endoderm, the mesoderm or the tissue derived from the mesoderm, and the ectoderm or the tissue derived from the ectoderm. Examples of the tissue derived from each germ layer include those described above.

According to the method for manufacturing of the present embodiment, all the germ layers of the endoderm, the mesoderm, and the ectoderm, or the tissue derived therefrom can be efficiently manufactured from the pluripotent stem cell without selecting the pluripotent stem cell in advance based on origin, establishment methods, the level of differentiation potential into the endoderm, the mesoderm, or the ectoderm, and the like of the pluripotent stem cell.

The step of differentiating the differentiation-promoted pluripotent stem cell is not particularly limited, and the step may be, for example, a method in which the embryoid body is formed and cultured, a method in which a predetermined gene is allowed to be expressed in the differentiation-promoted pluripotent stem cell, and the like.

EXAMPLES

Next, the present invention will be described in more detail by showing the examples, but the present invention is not limited to the following examples.

Experimental Example 1

(Examination of Culture Medium Inducing Differentiation-Promoted Pluripotent Stem Cell)

A combination of factors by which the expression level of the endoderm, mesoderm, and ectoderm markers can be increased while maintaining the undifferentiated state of the human pluripotent stem cell was examined.

Specifically, a 201B7 cell line which is human iPSC was cultured for 5 days in a normal culture medium (control), or in a culture medium containing the GSK3β inhibitor, the BMP signaling inhibitor, and the TGF-β inhibitor in various combinations. Next, the expression levels of the marker for undifferentiated cells, the endoderm marker, the mesoderm marker, and the ectoderm marker were measured by real time PCR. In addition, for comparison, expression levels of each marker in EB formed by being cultured in a culture medium for embryoid body (EB) formation for 36 days were also measured in the same manner.

CHIR99021 (CAS No. 252917-06-9) was used as the GSK3β inhibitor. In addition, Dorsomorphin (CAS No. 866405-64-3) was used as the BMP signaling inhibitor. Furthermore, SB431542 (CAS No. 301836-41-9) was used as the TGF-β inhibitor.

In addition, octamer-binding transcription factor 4 (OCT4) and NANOG genes were examined as the marker for undifferentiated cells. SOX1, PAX6, and NESTIN genes were examined as the ectoderm marker. A BRACHYURY gene was examined as the mesoderm marker. A SOX17 gene was examined as the endoderm marker.

Figure 1:
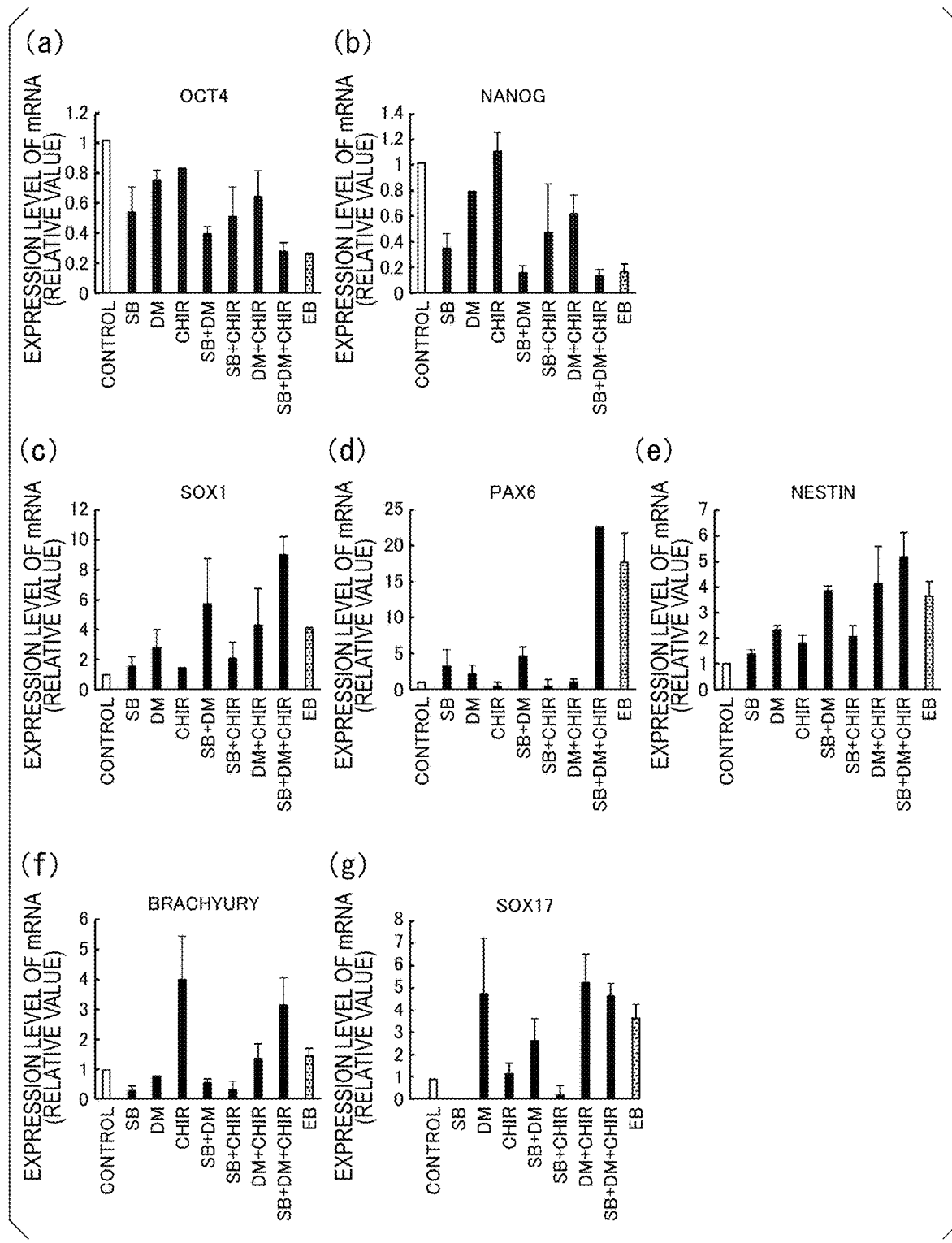

(a) to (g) of FIG. 1 are graphs showing an expression level of mRNA of each marker gene. (a) of FIG. 1 shows the level of expression of OCT4, (b) of FIG. 1 shows the level of expression of NANOG, (c) of FIG. 1 shows the level of expression of SOX1, (d) of FIG. 1 shows the level of expression of PAX6, (e) of FIG. 1 shows the level of expression of NESTIN, (f) of FIG. 1 shows the level of expression of BRACHYURY, and (g) of FIG. 1 shows the level of expression of SOX17.

In FIG. 1, SB represents SB431542, DM represents Dorsomorphin, and CHIR represents CHIR99021. In addition, SB+DM represents that SB and DM were added to the culture medium, SB+CHIR represents that SB and CHIR were added to the culture medium, DM+CHIR represents that DM and CHIR were added to the culture medium, and SB+DM+CHIR represents that SB, DM, and CHIR were added to the culture medium. The concentration of SB in the culture medium was 3 μM, the concentration of DM in the culture medium was 3 μM, and the concentration of CHIR in the culture medium was 3 μM.

As a result, it became clear that, in the case where SB, DM, and CHIR were added to the culture medium, the expression levels of the endoderm, mesoderm, and ectoderm markers can be increased while maintaining the undifferentiated state.

Experimental Example 2

(Examination of Condition Inducing Differentiation-Promoted Pluripotent Stem Cell)

A condition under which the human pluripotent stem cell was induced into the differentiation-promoted pluripotent stem cell was examined. More specifically, the 201B7 cell line which is human iPSC was cultured in the culture medium added with SB, DM, and CHIR for 3, 4, 5, or 6 days of culturing days, and the differentiation-promoted pluripotent stem cell was induced from the 201B7 cell line. As a control, the 201B7 cell line cultured in a normal culture medium for 6 days was used.

Next, the expression levels of the marker for undifferentiated cells, the endoderm marker, the mesoderm marker, and the ectoderm marker were measured by real time PCR. As the markers, the same genes as those of Experimental Example 1 were examined. In addition, the form of the cells was observed.

Figure 2:
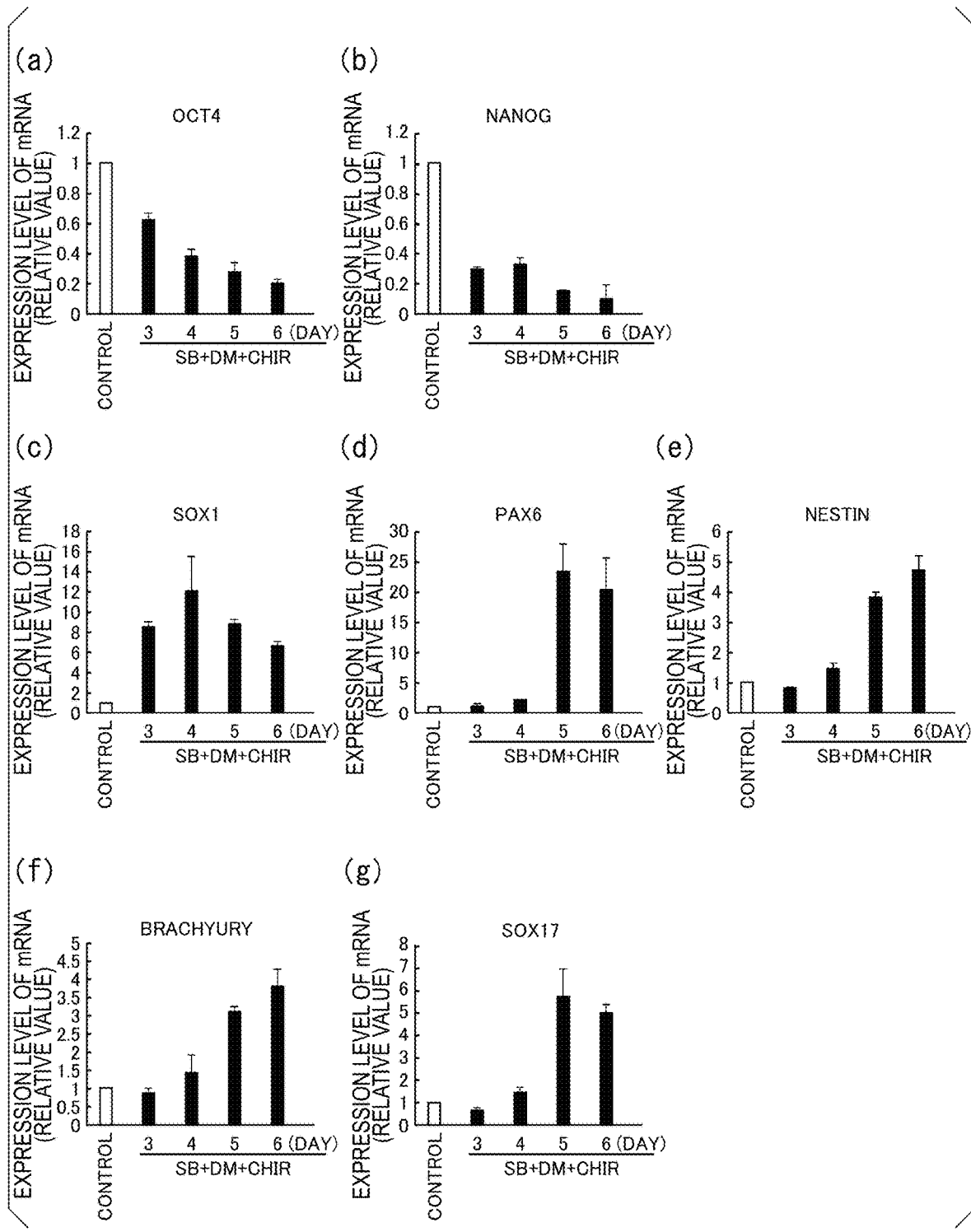

(a) to (g) of FIG. 2 are graphs showing an expression level of mRNA of each marker gene. (a) of FIG. 2 shows the level of expression of OCT4, (b) of FIG. 2 shows the level of expression of NANOG, (c) of FIG. 2 shows the level of expression of SOX1, (d) of FIG. 2 shows the level of expression of PAX6, (e) of FIG. 2 shows the level of expression of NESTIN, (f) of FIG. 2 shows the level of expression of BRACHYURY, and (g) of FIG. 2 shows the level of expression of SOX17.

As a result, it became clear that, by carrying out the culturing for 5 to 6 days with the culture medium added with SB, DM, and CHIR, the expression levels of the endoderm, mesoderm, and ectoderm markers can be increased while maintaining the undifferentiated state.

Figure 3:
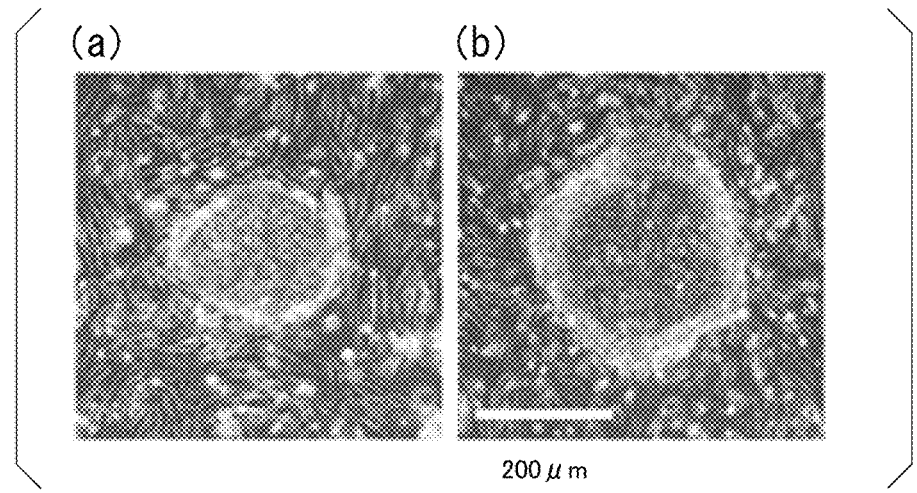

(a) and (b) of FIG. 3 are optical photomicrographs of a human pluripotent stem cell colony (hPSC colony). A scale bar indicates 200 μm. It can be determined that, based on the form of the cell of the hPSC colony shown in (a) of FIG. 3, the undifferentiated state is maintained in the cell. On the other hand, the cell of the hPSC colony shown in (b) of FIG. 3 has a form where a central part is recessed, and based on the form thereof, it can be determined that the cell excessively differentiated.

Figure 4:
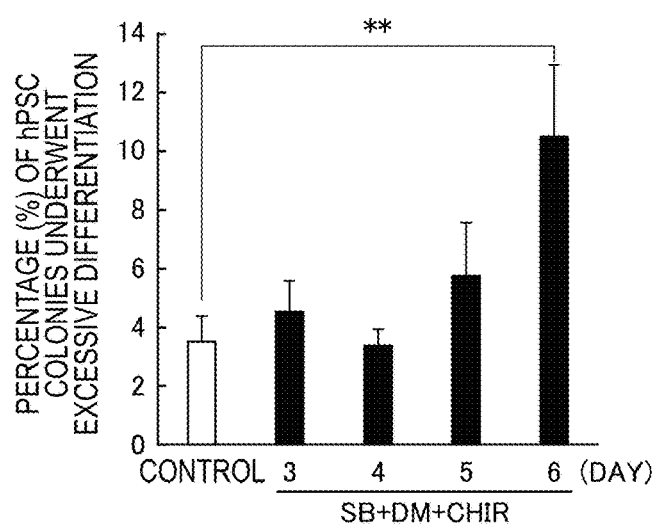

FIG. 4 is a graph showing a proportion of hPSC colonies underwent the excessive differentiation among expressed hPSC colonies in a case where the 201B7 cell line was cultured in the culture medium added with SB, DM, and CHIR for 3, 4, 5, or 6 days to induce the differentiation-promoted pluripotent stem cell. In FIG. 4, the symbol "**" indicates that there is a significant difference at a risk ratio of less than 0.1%.

As a result, it became clear that, in the case where the human pluripotent stem cell was cultured in the culture medium added with SB, DM, and CHIR for 6 days, the proportion of hPSC colonies underwent the excessive differentiation was significantly increased compared with the control.

Based on the above results, it became clear that, the condition under which the culturing was carried out in the culture medium added with SB, DM, and CHIR for 5 days is suitable as the condition under which the human pluripotent stem cell was induced into the differentiation-promoted pluripotent stem cell.

Experimental Example 3

(Property 1 of Differentiation-Promoted Pluripotent Stem Cell)

The inventors of the present invention have found that the colony of the differentiation-promoted pluripotent stem cells was smaller than a colony of a case in which a normal human pluripotent stem cell was cultured for the same period of time.

Specifically, the 201B7 cell line which is human iPSC was cultured in the culture medium added with SB, DM, and CHIR for 5 days to induce the differentiation-promoted pluripotent stem cell, and a change in diameter of the colony was measured. As a control, the 201B7 cell line was cultured in a normal culture medium for 5 days, and a change in diameter of the colony was measured. The experiments were independently carried out 3 times.

Figure 5:
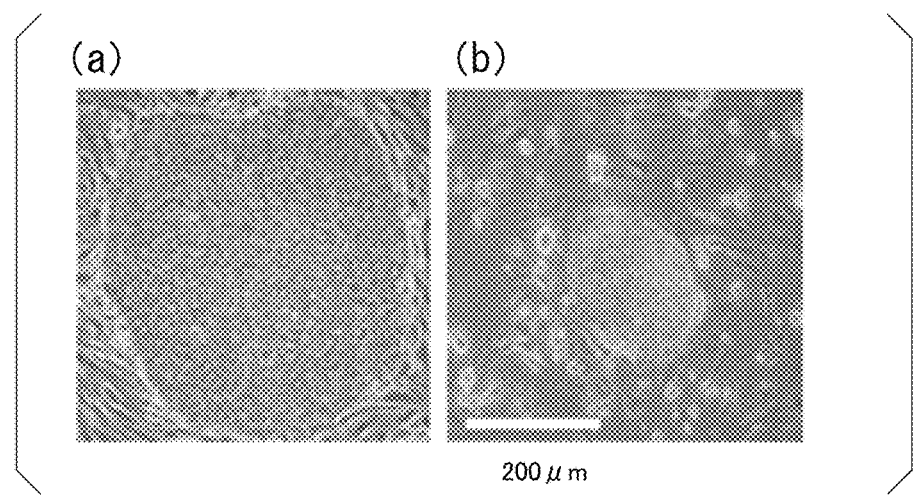

(a) of FIG. 5 is a representative photograph of the colony of the 201B7 cells cultured in the normal culture medium for 5 days. (b) of FIG. 5 is a photograph of the colony of the differentiation-promoted pluripotent stem cell induced by culturing the 201B7 cell line in the culture medium added with SB, DM, and CHIR for 5 days. Magnifications of both (a) of FIG. 5 and (b) of FIG. 5 are the same, and a scale bar shows 200 µm.

Figure 6:
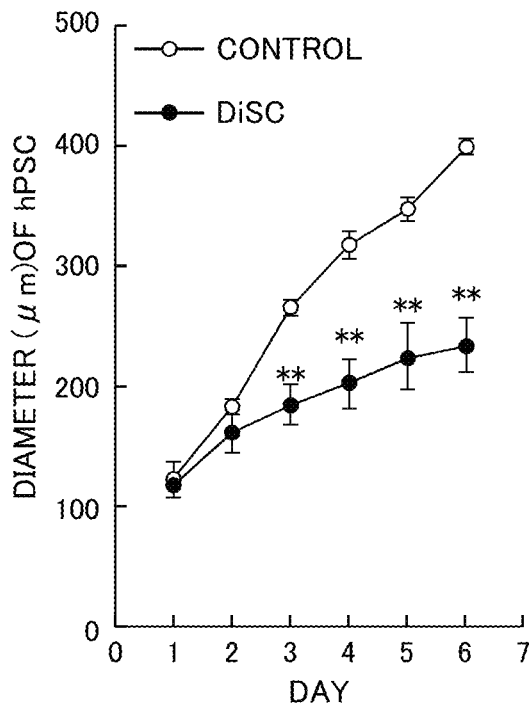
FIG. 6 is a graph showing the results of measuring changes in diameter of the differentiation-promoted pluripotent stem cell colony and a normal human pluripotent stem cell colony in Experimental Example 3.

As shown in (b) of FIG. 5, it became clear that the diameter of the colony of the differentiation-promoted pluripotent stem cells was smaller compared with the control. In addition, FIG. 6 is a graph showing the results of measuring changes in diameter of the differentiation-promoted pluripotent stem cell colony and a normal human pluripotent stem cell colony. In FIG. 5, the symbol "**" indicates that there is a significant difference at a risk ratio of less than 1%.

Based on the results of FIG. 6, it also became clear that, in the colony of the differentiation-promoted pluripotent stem cells, the diameter thereof after 3 days was significantly smaller compared with the colony of the normal human pluripotent stem cells.

Experimental Example 4

(Property 2 of Differentiation-Promoted Pluripotent Stem Cell)

The 201B7 cell line which is human iPSC was cultured in the culture medium added with SB, DM, and CHIR for 5 days, and therefore the differentiation-promoted pluripotent stem cell was formed. As a control, the 201B7 cell line cultured in a normal culture medium for 5 days was used.

Next, the expression levels of the endoderm marker, the mesoderm marker, and the ectoderm marker were measured by immunostaining. PAX6 and NESTIN proteins were detected as the ectoderm marker. In addition, BRACHYURY protein was detected as the mesoderm marker. Furthermore, SOX17 protein was examined as the endoderm marker.

Figure 7:
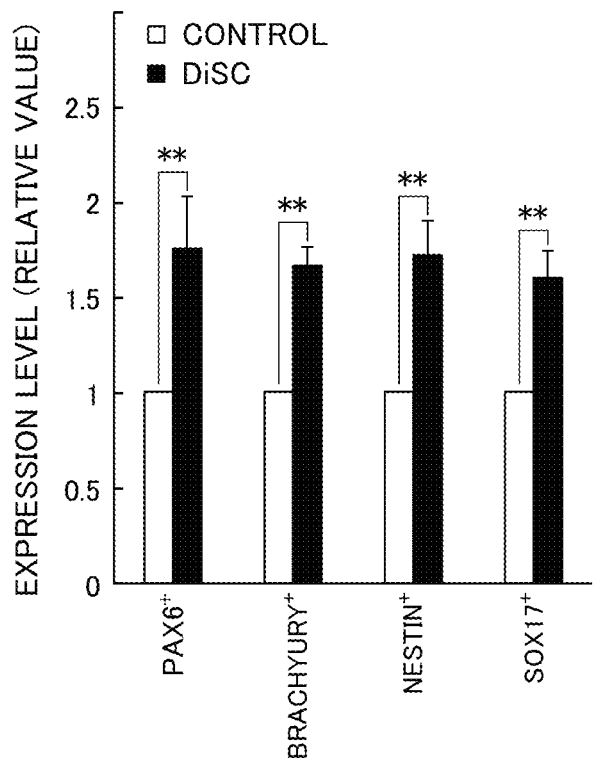
FIG. 7 is a graph showing expression levels of endoderm marker, mesoderm marker, and ectoderm marker proteins of the differentiation-promoted pluripotent stem cell and the normal human pluripotent stem cell in Experimental Example 4.

FIG. 7 is a graph showing an expression level of each marker protein. In FIG. 7, the symbol "**" indicates that there is a significant difference at a risk ratio of less than 0.1%. As a result, it was confirmed that, also in regard to the protein levels, the expression levels of the endoderm marker, the mesoderm marker, and the ectoderm marker were increased in the differentiation-promoted pluripotent stem cell compared with the control.

Next, the above-described differentiation-promoted pluripotent stem cells and the control cells were dissociated into cells one by one, the same marker as that in the above-described immunostaining was immunostained, and a ratio of the cell population expressing each marker protein was analyzed.

Figure 8:
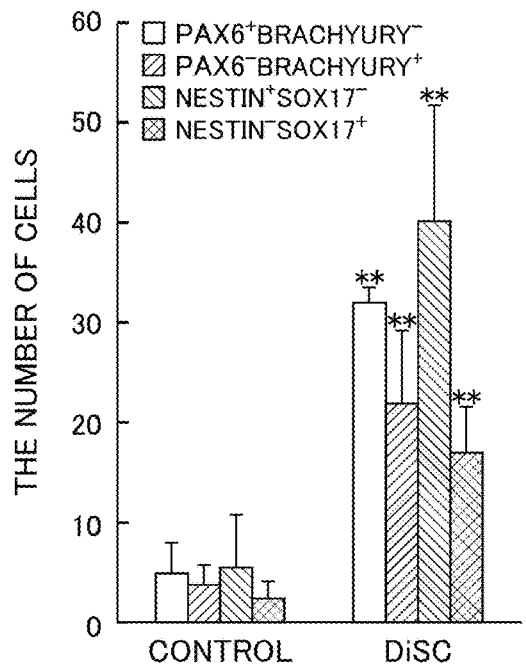
FIG. 8 is a graph showing the results of analysis of cell populations of the differentiation-promoted pluripotent stem cell and the normal human pluripotent stem cell in Experimental Example 4.

FIG. 8 is a graph showing the analysis results. As a result, it became clear that the number of $PAX6^+BRACHYURY^-$ cell, $PAX6^-BRACHYURY^+$ cell, $NESTIN^+SOX17^-$ cell, and $NESTIN^-SOX17^+$ cell was all increased in the differentiation-promoted pluripotent stem cell compared with the control.

Experimental Example 5

(Induction of Neural Stem Cell Mass from Differentiation-Promoted Pluripotent Stem Cell)

The 201B7 cell line which is human iPSC was cultured in the culture medium added with SB, DM, and CHIR for 5 days, and therefore the differentiation-promoted pluripotent stem cell was induced. Next, the differentiation-promoted pluripotent stem cells which were induced were dissociated into cells one by one, and the cells were cultured in a serum-free culture medium containing FGF2, Y27632 (CAS No. 331752-47-7), LIF, CHIR, and SB (hereinafter referred to as "NS culture medium" in some cases) for 5 days. Therefore, the neural stem cell mass (neurosphere, hereinafter referred to as "NS" in some cases) was formed (culturing days were a total of 10 days). Hereinafter, the neural stem cell mass (NS) formed through the differentiation-promoted pluripotent stem cell (DiSC) is referred to as "DiSC-NS" in some cases. The composition of the NS culture medium is shown in Table 1.

TABLE 1

| Composition of NS culture medium |
|---|
| 1:1 Mixture of DMEM culture medium and F-12 culture medium |
| 0.6% Glucose |
| 2 mM Glutamine |
| 3 mM Sodium bicarbonate |
| 5 mM HEPES |
| 25 µg/mL Insulin |
| 100 µg/mL Transferrin |
| 20 nM Progesterone |
| 30 nM Selenium chloride |
| 60 µM Putrescine |
| 2% B27 supplement (Thermo Fisher Scientific) |
| 20 ng/mL FGF2 |
| 10 µM Y-27632 (Wako Pure Chemical Industries) |
| 10 ng/mL hLIF |
| 3 µM CHIR99021 |
| 2 µM SB431542 |

The 201B7 cell line was cultured in a normal culture medium for 5 days, and then the cells were dissociated into cells one by one and cultured in the above-described NS culture medium for 5 days (culturing days were a total of 10 days) or for 10 days (culturing days was a total of 15 days), and the cells thus obtained were used as a control. Next, the number of neural stem cell mass formed was measured by microscopic observation. The experiments were independently carried out 3 times.

Figure 9:
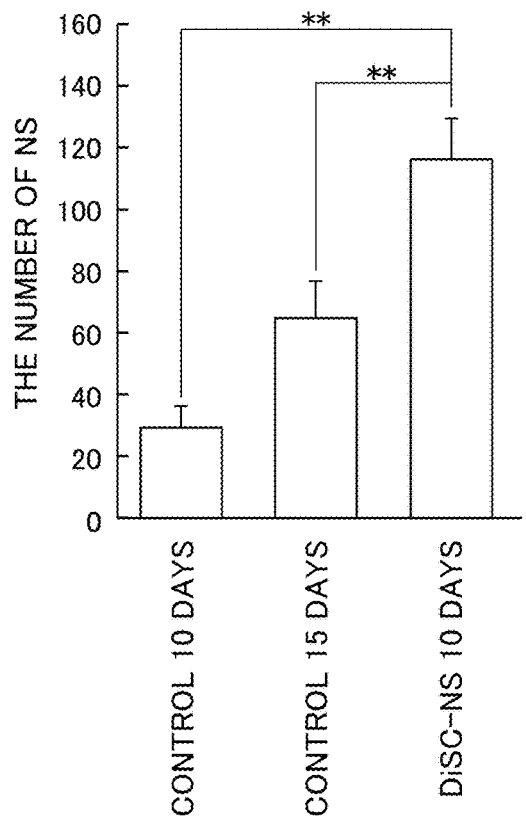
FIG. 9 is a graph showing the number of neural stem cell mass formed in Experimental Example 5.

FIG. 9 is a graph showing the number of neural stem cell mass formed by the culturing described above. In FIG. 9, the symbol "**" indicates that there is a significant difference at a risk ratio of less than 1%. As a result, it became clear that, if the neural stem cell mass is formed through the differentiation-promoted pluripotent stem cells, formation efficiency thereof is greatly improved.

Next, the expression levels of the marker for undifferentiated cells, the endoderm marker, the mesoderm marker, the ectoderm marker, and a neuron cell marker in the formed neural stem cell mass described above were measured by real time PCR.

OCT4 and NANOG genes were examined as the marker for undifferentiated cells. In addition, PAX6, SOX1, and NESTIN genes were examined as the ectoderm marker. Furthermore, βIII-tubulin (TUBB3) gene was examined as the neuron cell marker. Furthermore, BRACHYURY gene was examined as the mesoderm marker. Furthermore, SOX17 gene was examined as the endoderm marker.

(a) to (h) of FIG. 10 are graphs showing an expression level of mRNA of each marker gene. (a) of FIG. 10 shows the level of expression of OCT4, (b) of FIG. 10 shows the level of expression of NANOG, (c) of FIG. 10 shows the level of expression of PAX6, (d) of FIG. 10 shows the level of expression of SOX1, (e) of FIG. 10 shows the level of expression of NESTIN, (f) of FIG. 10 shows the level of expression of TUBB3, (g) of FIG. 10 shows the level of expression of BRACHYURY, and (h) of FIG. 10 shows the level of expression of SOX17. In FIG. 10, the symbol "**" indicates that there is a significant difference at a risk ratio of less than 1%.

As a result, it became clear that, in the neural stem cell mass formed through the differentiation-promoted pluripotent stem cell, the expression of the marker for undifferentiated cells was significantly reduced, and the expression of the ectoderm marker and the neuron cell marker was greatly increased.

Next, the above-described neural stem cell mass was dissociated into cells one by one, and the expression levels of the ectoderm marker, mesoderm marker, and endoderm marker proteins were examined by the analysis of cell populations. PAX6 and NESTIN proteins were detected as the ectoderm marker. In addition, BRACHYURY protein was detected as the mesoderm marker. Furthermore, SOX17 protein was detected as the endoderm marker.

(a) of FIG. 11 is a graph showing percentages of PAX6$^+$BRACHYURY$^+$ cell, PAX6$^+$BRACHYURY$^-$ cell, PAX6$^-$BRACHYURY$^+$ cell, and PAX6$^-$BRACHYURY$^-$ cell in a neural stem cell mass formed not through the differentiation-promoted pluripotent stem cells.

(b) of FIG. 11 is a graph showing percentages of PAX6$^+$BRACHYURY$^+$ cell, PAX6$^+$BRACHYURY$^-$ cell, PAX6$^-$BRACHYURY$^+$ cell, and PAX6$^-$BRACHYURY$^-$ cell in the neural stem cell mass formed through the differentiation-promoted pluripotent stem cells.

As a result, in the neural stem cell mass formed through the differentiation-promoted pluripotent stem cell, a percentage of the cells (PAX6$^+$BRACHYURY$^-$ cells) expressing only the ectoderm marker was high, whereas in the neural stem cell mass formed not through the differentiation-promoted pluripotent stem cell, a percentage of the cells (PAX6$^+$BRACHYURY$^-$ cells) expressing only the ectoderm marker was low and a percentage of the cells (PAX6$^-$BRACHYURY$^-$ cells) not expressing both the ectoderm marker and the mesoderm marker was high.

(a) of FIG. 12 is a graph showing percentages of NESTIN$^+$SOX17$^+$ cell, NESTIN$^+$SOX17$^-$ cell, NESTIN$^-$SOX17$^+$ cell, and NESTIN$^-$SOX17$^-$ cell in the neural stem cell mass formed not through the differentiation-promoted pluripotent stem cells. (b) of FIG. 12 is a graph showing percentages of NESTIN$^+$SOX17$^+$ cell, NESTIN$^+$SOX17$^-$ cell, NESTIN$^-$SOX17$^+$ cell, and NESTIN$^-$SOX17$^-$ cell in the neural stem cell mass formed through the differentiation-promoted pluripotent stem cells.

As a result, in the neural stem cell mass formed not through the differentiation-promoted pluripotent stem cell, a percentage of the cells (NESTIN$^+$SOX17$^+$ cells) expressing both the ectoderm marker and the endoderm marker was high compared with the neural stem cell mass formed through the differentiation-promoted pluripotent stem cell.

Experimental Example 6

(Examination 1 of Neurons after Differentiation Induction)

The neural stem cell mass was formed from the 201B7 cell line and WD39 cell line which are human iPSC, and KhES1cell line which is ES cell line, through the differentiation-promoted pluripotent stem cell, or not through the differentiation-promoted pluripotent stem cell. Furthermore, these neural stem cell mass were differentiated into the neurons. Hereinafter, the neuron obtained by differentiation of the neural stem cell mass thereinto, which is formed through the differentiation-promoted pluripotent stem cell is referred to as "DiSC neuron" in some cases. In addition, the neuron obtained by differentiation of the neural stem cell mass thereinto, which is formed not through the differentiation-promoted pluripotent stem cell was used as a control.

The differentiation into the neuron was carried out by seeding each neural stem cell mass on laminin- and poly-L-omithine-coated plates and culturing the cells in a neuronal differentiation-inducing culture medium. The composition of the neuronal differentiation-inducing culture medium is shown in Table 2.

TABLE 2

Composition of neuronal differentiation-inducing culture medium

1:1 Mixture of DMEM culture medium and F-12 culture medium
0.6% Glucose
2 mM Glutamine
3 mM Sodium bicarbonate
5 mM HEPES
25 µg/mL Insulin
100 µg/mL Transferrin
20 nM Progesterone
30 nM Selenium chloride
60 µM Putrescine
2% B27 supplement (Thermo Fisher Scientific)
10 ng/mL Brain-derived neurotrophic factor
(BDNF, R & D Systems)
10 ng/mL Glial cell-derived neurotrophic factor
(GDNF, R & D Systems)
200 µM Ascorbic acid
1 mM Dibutyryl-cAMP
10 µM DAPT (CAS No. 208255-80-5)

The expression levels of the neuron cell marker, a glutamatergic neuron marker, a GABAergic neuron marker, the marker for undifferentiated cells, the mesoderm marker, and the endoderm marker in the DiSC neuron and the control neuron were measured by real time PCR, 23 days after the culturing. In addition, for comparison, the expression levels of the marker genes in the human neural stem cell (hNSC) were measured in the same manner.

Microtubule-associated protein 2 (MAP2), synapsin-1 (SYN1), and βIII-tubulin (TUBB3) gene were examined as the neuron cell marker. Vesicular glutamate transporter 1 (VGLUT1) gene was examined as the glutamatergic neuron marker. Glutamic acid decarboxylase 2 (GAD65) and glutamic acid decarboxylase 1 (GAD67) genes were examined as the GABAergic neuron marker. NESTIN and SOX1 genes were examined as the ectoderm marker. OCT4 and NANOG genes were examined as the marker for undifferentiated cells. BRACHYURY gene was examined as the mesoderm marker. Furthermore, SOX17 gene was examined as the endoderm marker.

FIG. 13 is a graph showing an expression level of each marker gene. As a result, no clear tendency in the expression levels of these marker genes was recognized in the control neuron. On the other hand, in DiSC neuron, a tendency in which the expression levels of the neuron cell marker, the glutamatergic neuron marker, and the GABAergic neuron marker genes were high, and the expression levels of the ectoderm marker, the marker for undifferentiated cells, the mesoderm marker, and the endoderm marker genes were low, was recognized.

Experimental Example 7

(Examination 2 of Neurons after Differentiation Induction)

The DiSC neuron and the control neuron produced in Experimental Example 6 were immunostained, and examination was performed on maturation of the neurons. As an indicator of mature neurons, the number of synapsin-1$^+$βIII-tubulin$^+$ cells was measured. The experiments were independently carried out 3 times.

FIG. 14 is a graph showing measurement results. In FIG. 14, the symbol "*" indicates that there is a significant difference at a risk ratio of less than 1%. As a result, it became clear that the number of mature neurons was large in the DiSC neuron compared with the control neuron.

Experimental Example 8

(Examination 3 of Neurons after Differentiation Induction)

Using the microelectrode array, the DiSC neuron and the control neuron produced in Experimental Example 6 were electrophysically analyzed. More specifically, neuron functionality was evaluated by measuring the number of firing neurons per minute.

FIG. 15 is a graph showing the results of measuring the number of firing neurons in each neuron 11 to 23 days after the start of differentiation into neurons. The symbol "*" in FIG. 15 indicates that there is a significant difference at a risk rate of less than 5%, and the symbol "**" indicates that there is a significant difference at a risk rate of less than 1%.

As a result, it became clear that the number of firing neurons was significantly large in the DiSC neuron compared with the control neuron. This result indicates that the DiSC neuron contains more functional neurons compared with the control neuron.

Experimental Example 9

(Differentiation Induction of ES Cell Line Resistant to Differentiation into Neural Stem Cell Mass)

KhES2, KhES3, KhES4, and KhES5 which are human ES cell lines resistant to differentiation were differentiation-induced into the neural stem cell mass through the differentiation-promoted pluripotent stem cell.

Specifically, first, each cell line was cultured in the culture medium added with SB, DM, and CHIR for 5 days, and therefore the differentiation-promoted pluripotent stem cell was induced. Next, the differentiation-promoted pluripotent stem cells which were induced were dissociated into cells one by one, and the cells were cultured in the above-described NS culture medium for 10 days.

Cells which were differentiation-induced into the neural stem cell mass without through the differentiation-promoted pluripotent stem cell was used as a control. Hereinafter, the neural stem cell mass induced through the differentiation-promoted pluripotent stem cell is referred to as DdNS in some cases.

FIG. 16 shows optical photomicrographs of each cell cultured in the NS culture medium for 10 days. Magnifications of the photographs are all the same, and a scale bar shows 200 μm. In addition, FIG. 17 is a graph showing the results of measuring the number of neural stem cell mass in each cell. In FIG. 17, the symbol "**" indicates that there is a significant difference at a risk ratio of less than 1%.

As a result, it became clear that the neural stem cell mass can be efficiently induced even from the ES cells resistant to differentiation by being induced through the differentiation-promoted pluripotent stem cell.

Experimental Example 10

(Differentiation Induction of ES Cell Line Resistant to Differentiation into Neuron)

The differentiation into the neuron was carried out by seeding each neural stem cell mass induced in Experimental Example 9 on the laminin- and poly-L-ornithine-coated plates and culturing the cells in the above-described neuronal differentiation-inducing culture medium. Next, each neuron was immunostained on day 23 of culturing (on day 13 after culturing in the neuronal differentiation-inducing culture medium), and the number of βIII-tubulin$^+$MAP2$^+$ neurons occupying the whole neurons was measured. The experiments were independently carried out 3 times.

FIG. 18 is a graph showing measurement results. The symbol "*" in FIG. 18 indicates that there is a significant difference at a risk rate of less than 5%, and the symbol "**" indicates that there is a significant difference at a risk rate of less than 1%. As a result, it became clear that the number of βIII-tubulin$^+$MAP2$^+$ neurons was large in the neurons after differentiation induction through the DdNS compared with the control neuron.

In addition, each neuron was immunostained on day 23 of culturing (on day 13 after culturing in the neuronal differentiation-inducing culture medium), and the maturation of the neurons was examined. As an indicator of mature neurons, the number of synapsin-1$^+$βIII-tubulin$^+$ cells was measured. The experiments were independently carried out 3 times.

FIG. 19 is a graph showing measurement results. In FIG. 19, the symbol "**" indicates that there is a significant difference at a risk ratio of less than 1%. As a result, it became clear that the number of mature neurons was large in the neurons after differentiation induction through the DdNS compared with the control neuron.

Experimental Example 11

(Differentiation Induction into Neuron from TiPSC Immediately after Establishment)

It has been known that the TiPSC immediately after establishment is extremely difficult to differentiate into the neurons. Accordingly, in the same manner as in Experimental Example 10, a TiPSC 30 line immediately after new establishment was differentiated into the neurons by the method through DiSC and DdNS. Cells differentiated into the neurons without through DiSC and DdNS were used as a control. Next, each neuron was immunostained on day 23 of culturing (on day 13 after culturing in the neuronal differentiation-inducing culture medium), and the number of βIII-tubulin$^+$MAP2$^+$ neurons occupying the whole neurons was measured.

Note that the TiPSC line was established by introducing a Sendai virus vector (type "CytoTune™" of DNAVEC)

containing OCT4, SOX2, KLF4 and c-MYC in four vectors, respectively, into CD3-positive lymphocytes derived from healthy humans.

FIG. 20 is a graph showing measurement results. As a result, it became clear that the number of βIII-tubulin$^+$ MAP2$^+$ neurons was large in the neurons after differentiation induction by the method through DiSC and DdNS compared with the control neuron.

In addition, each neuron was immunostained on day 23 of culturing (on day 13 after culturing in the neuronal differentiation-inducing culture medium), and the maturation of the neurons was examined. As an indicator of mature neurons, the number of synapsin-1$^+$βIII-tubulin$^+$ cells was measured.

FIG. 21 is a graph showing measurement results. As a result, it became clear that the number of mature neurons was large in the neurons after differentiation induction by the method through DiSC and DdNS compared with the control neuron.

Table 3 shows the number of TiPSC lines showing the formation of the neural stem cell mass and the differentiation into the neurons by the method not through DiSC and DdNS (control) and the method through DiSC and DdNS (shown as "DdNS" in Table 3). By the method through DiSC and DdNS, the TiPSC line immediately after establishment, which has been known to be extremely difficult to differentiate into the neurons, could be differentiated into the neurons with high efficiency.

TABLE 3

|  | Control | DdNS |
|---|---|---|
| The number of TiPSC lines which formed neural stem cell mass | 9 | 29 |
| The number of TiPSC differentiated into neurons | 7 | 28 |
| Percentage (%) of TiPSC lines differentiated into neurons | 23.3 (7/30) | 93.3 (28/30) |

Experimental Example 12

(Examination of Differentiation Induction into Dopaminergic Neuron)

In the same manner as in Experimental Example 10, the 201B7 cell line and the WD39 cell line which are human iPSC, and the KhES1cell line which is the ES cell line were differentiation-induced into the neurons by the method through DiSC and DdNS.

In addition, the 201B7 cell line and the WD39 cell line which are human iPSC, and the KhES1cell line which is the ES cell line were differentiation-induced into the dopaminergic neurons. Specifically, each cell was cultured in the culture medium added with SB, DM, and CHIR for 5 days, and therefore the differentiation-promoted pluripotent stem cell was induced. Next, the differentiation-promoted pluripotent stem cells which were induced were dissociated into cells one by one, and the cells were cultured in the above-described NS culture medium for 3 days. Next, the above-described culture medium was further added with CHIR (3 µM), Shh (100 ng/mL), Purmorpamine (CAS No. 483367-10-8) (2 µM), and the culturing was performed for 7 days. Therefore, the cultured cells were differentiated into dopaminergic neuron progenitor cells. Next, TGF-β3 (1 ng/mL) and CHIR (3 µM) were added to the above-described neuronal differentiation-inducing culture medium, and culturing was performed for 3 days. Then, culturing was performed under conditions where CHIR was removed to differentiate the cultured cells into the dopaminergic neurons.

Next, expression levels of tyrosine hydroxylase (TH) which is a dopaminergic neuron marker, and βIII-tubulin which is a neuron cell marker, were examined by immunostaining. Cells differentiation-induced into the neurons without through DiSC and DdNS were used as a control.

FIG. 22 is a graph showing the results of measuring percentages of βIII-tubulin$^+$ cell or TH$^+$βIII-tubulin$^+$ cell. In FIG. 22, DdNS shows results of the neurons after induction in the same manner as in Experimental Example 10. In addition, DdNS (Dopa) shows results of the dopaminergic neurons induced by the above-described method. Furthermore, the symbol "**" indicates that there is a significant difference at a risk ratio of less than 1%.

As a result, it became clear that the differentiation induction into the dopaminergic neuron can be carried out with high efficiency by the method through DiSC and DdNS.

Experimental Example 13

(Examination of Differentiation Potential of Differentiation-Promoted Pluripotent Stem Cell Derived from iPSC into Three Germ Layers)

The differentiation potential of the differentiation-promoted pluripotent stem cell (DiSC) induced from iPSC into the three germ layers was examined. Specifically, the 201B7 cell line which is human iPSC was cultured in the culture medium added with SB, DM, and CHIR for 5 days, and therefore the differentiation-promoted pluripotent stem cell was formed. Final concentrations of SB, DM, and CHIR were all 3 µM. As a control, the 201B7 cell line cultured in a normal culture medium for 5 days was used.

Next, the colony of the differentiation-promoted pluripotent stem cells was dissociated into cells one by one. A dissociation solution containing 0.25% trypsin, 100 µg/mL collagenase IV, 1 mM calcium chloride, 20% KnockOut Serum Replacement (KSR, Invitrogen) was used for cell dissociation.

Next, SNL feeder cells (CELL BIOLABS) were removed from the differentiation-promoted pluripotent stem cells which were dissociated. The cells were suspension-cultured in a culture dish for 8 days using a culture medium from which FGF2 was removed from a culture medium for normal human ES cells, and therefore embryoid bodies (hereinafter referred to as "EB" in some cases) were formed. Half of the culture medium was changed every other day.

Thereafter, the EB on day 8 was adhered as it was to Matrigel-coated 96-well plate without breaking, and was adhesive cultured for 10 days. The culture medium from which FGF2 was removed from the culture medium for normal human ES cells was used as a culture medium. The culture medium was exchanged every other day.

Next, the cells were fixed 10 days after the start of the adhesive culture (18 days after the formation of the differentiation-promoted pluripotent stem cell). Next, the fixed cells were immunostained to detect AFP which is a differentiation marker of the endoderm, αSMA which is a differentiation marker of the mesoderm, and βIII-tubulin which is a differentiation marker of the ectoderm. Therefore, the differentiation potential into the three germ layers was examined. IN Cell Analyzer 6000 (GE Healthcare Bioscience) was used for photographing of photomicrographs of cells and quantification of fluorescence intensity.

FIG. 23 is a graph showing the results of quantifying an expression level of differentiation markers in each cell. In FIG. 23, the term "DiSC" indicates results of cells obtained by differentiation of the EB which was formed through DiSC. In addition, the symbol "**" indicates that there is a significant difference at a risk ratio of less than 0.1%. As a result, it became clear that the differentiation potential of the cells obtained by differentiation of the EB which was formed from iPSC through DiSC, into the three germ layer was significantly improved as compared with the control cells.

Experimental Example 14

(Examination of Differentiation Potential of Differentiation-Promoted Pluripotent Stem Cell Derived from ES Cell Resistant to Differentiation, into Three Germ Layers)

The differentiation potential of the differentiation-promoted pluripotent stem cell induced from the ES cell line resistant to differentiation, into the three germ layers was examined. KhES2, KhES3, KhES4, and KhES5 which are the human ES cell lines were used as the ES cell line resistant to differentiation.

First, each ES cell line was cultured in the culture medium added with SB, DM, and CHIR for 5 days, and therefore the differentiation-promoted pluripotent stem cell was formed. Final concentrations of SB, DM, and CHIR were all 3 μM. As a control, each ES cell line cultured in a normal culture medium for 5 days was used.

Next, the expression levels of the endoderm marker, the mesoderm marker, and the ectoderm marker were measured by immunostaining. SOX1 protein was detected as the ectoderm marker. In addition, BRACHYURY protein was detected as the mesoderm marker. Furthermore, SOX17 protein was examined as the endoderm marker.

(a) to (c) of FIG. 24 are graphs showing an expression level of each marker protein. (a) of FIG. 24 is a graph showing the expression level of SOX1 protein, (b) of FIG. 24 is a graph showing the expression level of BRACHYURY protein, and (c) of FIG. 24 is a graph showing the expression level of SOX17 protein. In (a) to (c) of FIG. 24, the term "DiSC" indicates results of the differentiation-promoted pluripotent stem cells. In addition, the symbol "**" indicates that there is a significant difference at a risk ratio of less than 0.1%. As a result, it was confirmed that, the expression levels of the ectoderm marker, the mesoderm marker, and the endoderm marker were significantly increased in the differentiation-promoted pluripotent stem cell compared with the control.

Next, in the same manner as in Experimental Example 13, the colony of each differentiation-promoted pluripotent stem cell was dissociated into cells one by one. The cells were cultured for 8 days, and therefore the EB was formed. Furthermore, in the same manner as in Experimental Example 13, the EB was adhered to Matrigel-coated 96-well plate, and was adhesive cultured for 10 days.

Next, the cells were fixed 10 days after the start of the adhesive culture (18 days after the formation of the differentiation-promoted pluripotent stem cell). Next, the fixed cells were immunostained to detect AFP which is a differentiation marker of the endoderm, αSMA which is a differentiation marker of the mesoderm, and βIII-tubulin which is a differentiation marker of the ectoderm. Therefore, the differentiation potential into the three germ layers was examined. IN Cell Analyzer 6000 (GE Healthcare Bioscience) was used for photographing of photomicrographs of cells and quantification of fluorescence intensity.

FIG. 25 is a graph showing the results of quantifying an expression level of differentiation markers in each cell. In FIG. 25, the term "DiSC" indicates results of cells obtained by differentiation of the EB which was formed through DiSC. As a result, it became clear that the differentiation potential of the cells obtained through the differentiation-promoted pluripotent stem cells, into the three germ layer was significantly improved as compared with the control cells.

Experimental Example 15

(Examination of Differentiation Potential of Differentiation-Promoted Pluripotent Stem Cell Derived from TiPSC Immediately after Establishment, into Three Germ Layers)

The differentiation potential of the differentiation-promoted pluripotent stem cell induced from TiPSC immediately after establishment, into the three germ layers was examined. As TiPSC, the human TiPSC 30 line immediately after establishment in the same manner as in Experimental Example 11 without colony screening was used.

First, each TiPSC line was cultured in the culture medium added with SB, DM, and CHIR for 5 days, and therefore the differentiation-promoted pluripotent stem cell was formed. The final concentrations of SB, DM, and CHIR were all 3 μM. As a control, each TiPSC line cultured in a normal culture medium for 5 days was used.

Next, the expression levels of the endoderm marker, the mesoderm marker, and the ectoderm marker were measured by immunostaining. SOX1 protein was detected as the ectoderm marker. In addition, BRACHYURY protein was detected as the mesoderm marker. Furthermore, SOX17 protein was examined as the endoderm marker.

(a) to (c) of FIG. 26 are graphs showing an expression level of each marker protein. (a) of FIG. 26 is a graph showing the expression level of SOX1 protein, (b) of FIG. 26 is a graph showing the expression level of BRACHYURY protein, and (c) of FIG. 26 is a graph showing the expression level of SOX17 protein. In (a) to (c) of FIG. 26, a lateral axis indicates numbers of TiPSC lines. The numbers in the graphs are relative to the expression level in the control cell where the expression level in the control cell is 1.

As a result, it was confirmed that, the expression levels of the ectoderm marker, the mesoderm marker, and the endoderm marker were significantly increased in the differentiation-promoted pluripotent stem cell induced from TiPSC immediately after establishment compared with the control.

INDUSTRIAL APPLICABILITY

According to the present invention, it is possible to provide a technique in which even the ES cell line showing the resistance to differentiation, and the iPS cell line immediately after establishment, which has not been selected by selection of cell lines can be effectively differentiated into a desired cell.

The invention claimed is:
1. A cell culture comprising:
(i) a differentiation-promoted pluripotent stem cell,
(ii) a pluripotent stem cell; and
(iii) a culture medium comprising:
a glycogen synthase kinase 3β (GSK3β) inhibitor,
a bone morphogenic protein (BMP) signaling inhibitor, and
a transforming growth factor (TGF)-β inhibitor;
wherein the differentiated pluripotent-promoted stem cell is obtained from a pluripotent stem cell comprising an embryonic stem (ES) cell line resistant to differentiation or an induced pluripotent stem (iPS) cell produced from a mature T cell (TiPSC) without selection of suitable clones according to origin, or a level of differentiation potential after establishment, wherein the differentiation-promoted pluripotent stem cell is obtained from the ES cell line resistant to differentiation or the iPS cell after 4-6 days; and wherein the differentiation-promoted pluripotent stem cell has increased expression levels of endoderm and mesoderm markers when compared to control cells, while an undifferentiated state is maintained.

2. A method for manufacturing a differentiation-promoted pluripotent stem cell, comprising:

culturing a pluripotent stem cell for 4-6 days in a culture medium to obtain a differentiation-promoted pluripotent stem cell wherein the culture medium comprises, as active ingredients:

a Glycogen synthase kinase 3β (GSK3B) inhibitor;

a Bone morphogenic protein (BMP) signaling inhibitor; and a Transforming growth factor (TGF)-β inhibitor;

wherein the pluripotent stem cell is an embryonic stem (ES) cell line resistant to differentiation or an induced pluripotent stem cell (iPSC) produced from a mature T cell (TiPSC) and has not been selected as a suitable clone in advance according to origin, or a level of differentiation potential into endoderm or mesoderm, wherein the differentiation-promoted pluripotent stem cell is a cell in which expression levels of endoderm marker and mesoderm marker are increased when compared with that of control cells, while an undifferentiated state is maintained.

3. The culture according to claim 1, wherein the ES cell line is selected from the group consisting of KhES2, KhES3, KhES4, and KhES5.

4. The method of claim 2, wherein the ES cell line is selected from the group consisting of KhES2, KhES3, KhES4, and KhES5.

5. The culture according to claim 1, wherein the GSK3β inhibitor is present at 3 µM, the BMP signaling inhibitor is present at 3-6 µM, and the TGF-β inhibitor is present at 3-6 µM.

6. The culture according to claim 1, wherein GSK3β inhibitor is CHIR99021, the BMP signaling inhibitor is selected from dorsomorphin, LDN and noggin and the TGF-β inhibitor is selected from SB431542 and A-83-01.

7. The method according to claim 2, wherein the GSK3β inhibitor is present at 3 µM, the BMP signaling inhibitor is present at 3-6 µM, and the TGF-β inhibitor is present at 3-6 µM.

8. The method according to claim 2, wherein GSK3β inhibitor is CHIR99021, the BMP signaling inhibitor is selected from dorsomorphin, LDN and noggin and the TGF-β inhibitor is selected from SB431542 and A-83-01.

* * * * *